US009956171B2

(12) United States Patent
Spargo et al.

(10) Patent No.: US 9,956,171 B2
(45) Date of Patent: May 1, 2018

(54) LIQUID INHALATION FORMULATION COMPRISING RPL554

(71) Applicant: VERONA PHARMA PLC, Cardiff (GB)

(72) Inventors: Peter Lionel Spargo, Canterbury (GB); Edward James French, Canterbury (GB); Phillip A. Haywood, Buntingford (GB)

(73) Assignee: VERONA PHARMA PLC, Cardiff (GB)

(*) Notice: Subject to any disclaimer, the term of this patent is extended or adjusted under 35 U.S.C. 154(b) by 0 days. days.

(21) Appl. No.: 15/509,943

(22) PCT Filed: Sep. 15, 2015

(86) PCT No.: PCT/GB2015/052668
§ 371 (c)(1),
(2) Date: Mar. 9, 2017

(87) PCT Pub. No.: WO2016/042313
PCT Pub. Date: Mar. 24, 2016

(65) Prior Publication Data
US 2017/0239178 A1    Aug. 24, 2017

(30) Foreign Application Priority Data

Sep. 15, 2014 (GB) .................. 1416274.7
Mar. 19, 2015 (GB) .................. 1504662.6

(51) Int. Cl.
A61K 31/519    (2006.01)
A61K 9/00      (2006.01)
A61K 47/26     (2006.01)
A61K 47/02     (2006.01)

(52) U.S. Cl.
CPC .......... A61K 9/0078 (2013.01); A61K 31/519 (2013.01); A61K 47/02 (2013.01); A61K 47/26 (2013.01)

(58) Field of Classification Search
CPC .... A61K 9/0078; A61K 31/519; A61K 47/02; A61K 47/26
USPC ....................................................... 514/267
See application file for complete search history.

(56) References Cited

U.S. PATENT DOCUMENTS

| 6,630,169 | B1 * | 10/2003 | Bot ...................... A61K 9/0043 424/426 |
| 6,794,391 | B2 | 9/2004 | Oxford et al. |
| 7,105,663 | B2 | 9/2006 | Oxford et al. |
| 7,378,424 | B2 | 5/2008 | Oxford et al. |
| 7,524,834 | B2 | 4/2009 | Karlsson et al. |
| 8,242,127 | B2 | 8/2012 | Oxford et al. |
| 9,062,047 | B2 | 6/2015 | Walker et al. |
| 9,700,558 | B2 * | 7/2017 | Walker ................... A61K 45/06 |
| 9,717,732 | B2 | 8/2017 | Walker et al. |
| 2003/0036542 | A1 | 2/2003 | Oxford et al. |
| 2004/0171828 | A1 | 9/2004 | Oxford et al. |
| 2004/0176353 | A1 | 9/2004 | Oxford et al. |
| 2008/0206163 | A1 | 8/2008 | Oxford et al. |
| 2008/0226736 | A1 | 9/2008 | Caponetti et al. |
| 2013/0225616 | A1 | 8/2013 | Walker et al. |
| 2016/0000790 | A1 | 1/2016 | Walker et al. |
| 2016/0008363 | A1 | 1/2016 | Walker et al. |
| 2017/0112839 | A1 | 4/2017 | Abbott-Banner et al. |

FOREIGN PATENT DOCUMENTS

| WO | 95/31964 A1 | 11/1995 |
| WO | 00/58308 A1 | 10/2000 |
| WO | 2012/020016 A1 | 2/2012 |
| WO | 2014/037727 A1 | 3/2014 |
| WO | 2014/140647 A1 | 9/2014 |
| WO | 2014/140648 A1 | 9/2014 |
| WO | 2015/173551 A1 | 11/2015 |
| WO | 2016/128742 A1 | 8/2016 |

OTHER PUBLICATIONS

Franciosi et al., "Efficacy and safety of RPL554, a dual PDE3 and PDE4 inhibitor, in healthy volunteers and in patients with asthma or chronic obstructive pulmonary disease: findings from four clinical trials", The Lancet: Respiratory Medicine, Nov. 2013, vol. 1, No. 9, pp. 714-727.
Calzetta et al., "Effect of the Mixed Phosphodiesterase 3/4 Inhibitor RPL554 on Human Isolated Bronchial Smooth Muscle Tone", The Journal of Pharmacology and Experimental Therapeutics, Sep. 2013, vol. 346, No. 3, pp. 414-423.
Compton et al., "The Novartis view on emerging drugs and novel targets for the treatment of chronic obstructive pulmonary disease", Pulmonary Pharmacology & Therapeutics, 2013, vol. 26, No. 5, pp. 562-573.
Boswell-Smith et al., The Pharmacology of Two Novel Long-Acting Phosphodiesterase 3/4 Inhibitors, RPL554 [9,10-Dimethoxy-2(2,4,6-trimethylphenylimino)-3-(N-carbamoyl-2-aminoethyl)-3,4,6,7-tetrahydro-2H-pyrimido[6,1-a] isoquinolin-4-one] and RPL565 [6,7-Dihydro-2-(2,6-diisopropylphenoxy)-9,10-dimethoxy-4H-pyrimido[6,1-a] isoquinolin-4-one], The Journal of Pharmacology and Experimental Therapeutics, 2006, vol. 318, No. 2, pp. 840-848.
Jadwiga A. Wedzicha, "Dual PDE 3/4 inhibition: a novel approach to airway disease?", The Lancet: Respiratory Medicine, 2013, vol. 1, No. 9, pp. 669-670.

(Continued)

Primary Examiner — Sreenivasan Padmanabhan
Assistant Examiner — Y Jeanmarie Z Calvillo
(74) Attorney, Agent, or Firm — MH2 Technology Law Group, LLP

(57) ABSTRACT

The present invention relates to a liquid pharmaceutical composition suitable for administration by inhalation which comprises a diluent and a suspension of particles of 9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one (RPL554) or a pharmaceutically acceptable salt thereof. Also described is a liquid pharmaceutical composition according to the invention for use in the treatment of the human or animal body.

18 Claims, 3 Drawing Sheets

(56) References Cited

OTHER PUBLICATIONS

Ukena et al., "Effects of the mixed phosphodiesterase III/IV inhibitor, zardaverine, on airway function in patients with chronic airflow obstruction", Respiratory Medicine, 1995, vol. 89, No. 6, pp. 441-444.

Grootendorst et al., "Reduction in sputum neutrophil and eosinophil numbers by the PDE4 inhibitor roflumilast in patients with COPD", Thorax, 2007, vol. 62, No. 12, pp. 1081-1087.

* cited by examiner

LIQUID INHALATION FORMULATION COMPRISING RPL554

CROSS-REFERENCE TO RELATED APPLICATIONS

This application is a U.S. National Stage application of PCT/GB2015/052668 filed 15 Sep. 2015, which claims priority to Great Britain Application No. 1416274.7 filed 15 Sep. 2014, and Great Britain Application No. 1504662.6 filed 19 Mar. 2015, the entire disclosures of which are hereby incorporated by reference in their entireties.

FIELD OF THE INVENTION

The present invention relates to a liquid pharmaceutical composition comprising a respiratory drug.

BACKGROUND OF THE INVENTION

The toxicokinetic properties of liquid pharmaceutical compositions are unpredictable. It is important that an active pharmaceutical ingredient (API) is correctly formulated so that a safe, effective and controlled dosage is provided when the composition is delivered to a patient. This is particularly the case for inhaled compositions. Furthermore, liquid pharmaceutical compositions must have reliable long term stability to ensure that the dosage profile of the composition will be maintained after storage. This avoids the administration of incorrect dosages. Pharmaceutical compositions must also be formulated in such a way that administration is not unpleasant for a patient, for instance as regards taste and acidity.

RPL554 (9,10-Dimethoxy-2-(2,4,6-trimethylphenylimino)-3-(N-carbamoyl-2-aminoethyl)-3,4,6,7-tetrahydro-2H-pyrimido[6,1-a]isoquinolin-4-one) is a dual PDE3/PDE4 inhibitor and is described in WO 00/58308 (and is also sometimes referred to as RPL554). As a combined PDE3/PDE4 inhibitor, RPL554 has both anti-inflammatory and bronchodilatory activity and is useful in the treatment of respiratory disorders such as asthma and chronic obstructive pulmonary disease (COPD). The structure of RPL554 is shown below.

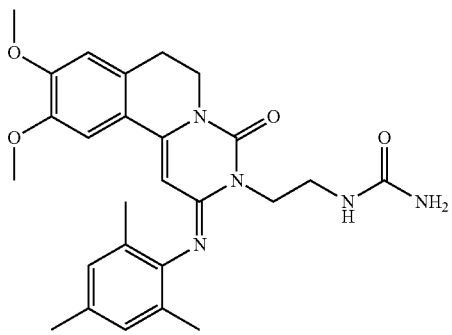 [SMILES: COc1cc2c(cc1OC)-c1c/c(=N\c3c(C)cc(C)cc3C)n(CCNC(N)=O)c(=O)n1CC2]

It is often preferable to administer RPL554 by inhalation because of its efficacy in the treatment of respiratory disorders. An effective method of administration is nebulisation. Franciosi et al. disclose a solution of RPL554 in a citrate-phosphate buffer (Efficacy and safety of RPL554, a dual PDE3 and PDE4 inhibitor, in healthy volunteers and in patients with asthma or chronic obstructive pulmonary disease: findings from four clinical trials, The Lancet: Respiratory Medicine November 2013; 1(9):714-27. DOI: 10.1016/S2213-2600(13)70187-5).

SUMMARY OF THE INVENTION

It is a surprising finding of the present invention that the optimal composition for inhalation comprising RPL554 is a liquid pharmaceutical composition comprising a suspension of particles of RPL554. Suspensions of RPL554 have been found to have highly desirable properties for a clinical setting. A number of benefits have been found to be associated with a liquid pharmaceutical composition which comprises a diluent and a suspension of particles of RPL554 or a pharmaceutically acceptable salt thereof.

The liquid pharmaceutical composition of the invention has greatly improved properties over previous formulations, for instance when compared with a solution formulation of RPL554. Regarding toxicokinetic properties, the suspension formulation has been found to have delayed release characteristics compared to those of a solution. This can reduce the number of treatments that must be administered to a patient. The suspension has also been found to allow a much greater dosage of RPL554 to be administered, as can be seen from plasma $C_{max}$ and AUC values. This can also reduce the frequency of administrations required.

The liquid pharmaceutical composition of the invention also shows excellent stability, with compositions showing no degradation after 12 months at ambient conditions (25° C.), nor after 6 months at accelerated conditions (40° C.). Degradation is observed in a comparable solution composition under the same conditions. The compositions may show no degradation after 12 months at ambient conditions (25° C./60% RH), nor after 6 months at accelerated conditions (40° C./75% RH).

Accordingly, the present invention provides a liquid pharmaceutical composition comprising a diluent and a suspension of particles of 9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one (RPL554) or a pharmaceutically acceptable salt thereof.

The invention also provides a liquid pharmaceutical composition according to the invention for use in the treatment of the human or animal body. A liquid pharmaceutical composition according to the invention may be used in the treatment or prevention of a disease or condition selected from asthma, allergic asthma, hay fever, allergic rhinitis, bronchitis, emphysema, bronchiectasis, chronic obstructive pulmonary disease (COPD), adult respiratory distress syndrome (ARDS), steroid resistant asthma, severe asthma, paediatric asthma, cystic fibrosis, lung fibrosis, pulmonary fibrosis, interstitial lung disease, skin disorders, atopic dermatitis, psoriasis, ocular inflammation, cerebral ischaemia, inflammatory diseases and auto-immune diseases.

Typically, said disease or condition is asthma or COPD, more typically COPD.

The invention also provides a method of treating or preventing a disease or condition as defined herein in a subject, which method comprises administering to said subject an effective amount of a liquid pharmaceutical composition according according to the invention.

Figure 2:
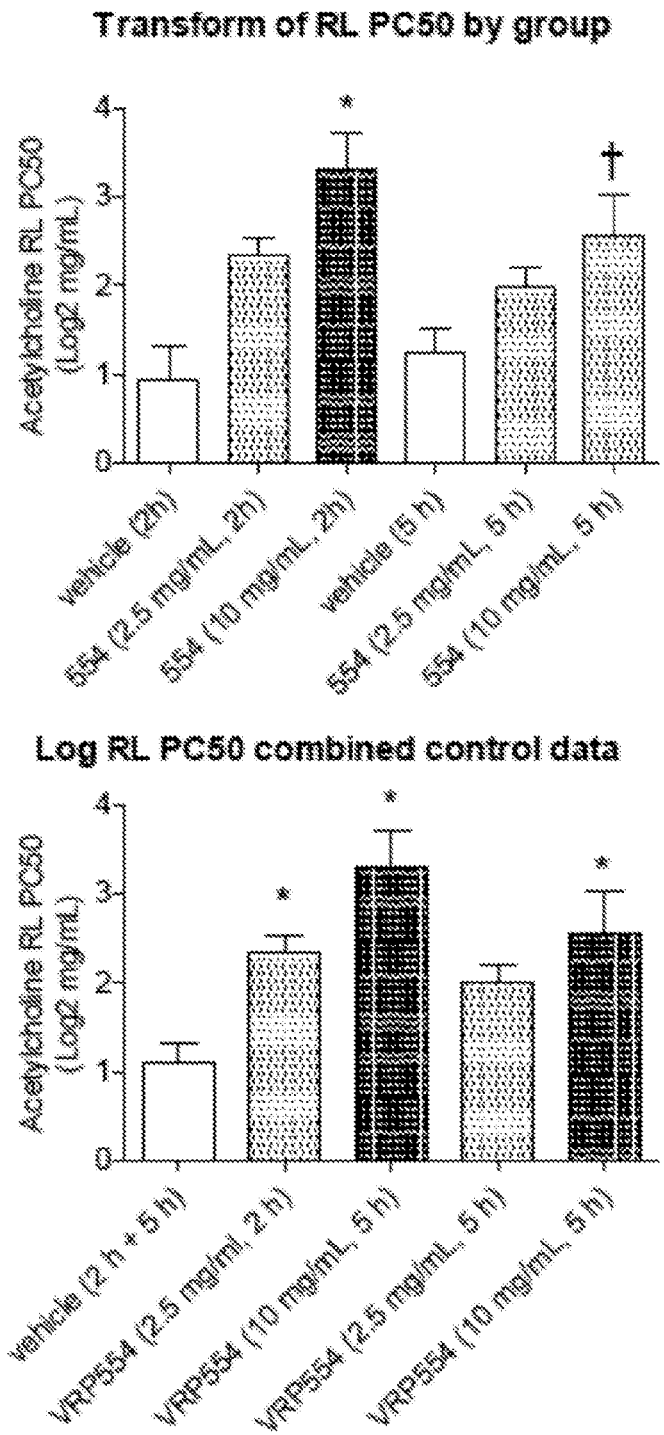

FIG. 2—Acetylcholine RL PC50 in animals treated with vehicle or the RPL554 suspension formulation: 2 and 5 h time point: Acetylcholine RL PC50 was log transformed for the purposes of statistical analysis (upper panel). Non parametric analysis did show a significant difference between 2 h (10 mg/mL RPL554 suspension, P=0.0268 unadjusted) vs vehicle control group. Re-analysis of the data by combining the vehicle data (2+5 h), revealed an overall significant bronchoprotection (P=0.0016) which was reflected by a significant degree of bronchoprotection with 2.5 mg/mL RPL554 suspension (2.52 fold (1-5.72), P<0.05 and 10 mg/mL RPL554 suspension (4.67 fold (2-11), *P<0.05) vs vehicle. At the 5 h time point, RPL554 10 mg/mL suspension caused a significant degree of bronchoprotection (2.77 fold (1.3-6.0), *P<0.05). (N=8,4,4,3, 6, left to right) (lower panel).

Figure 3:
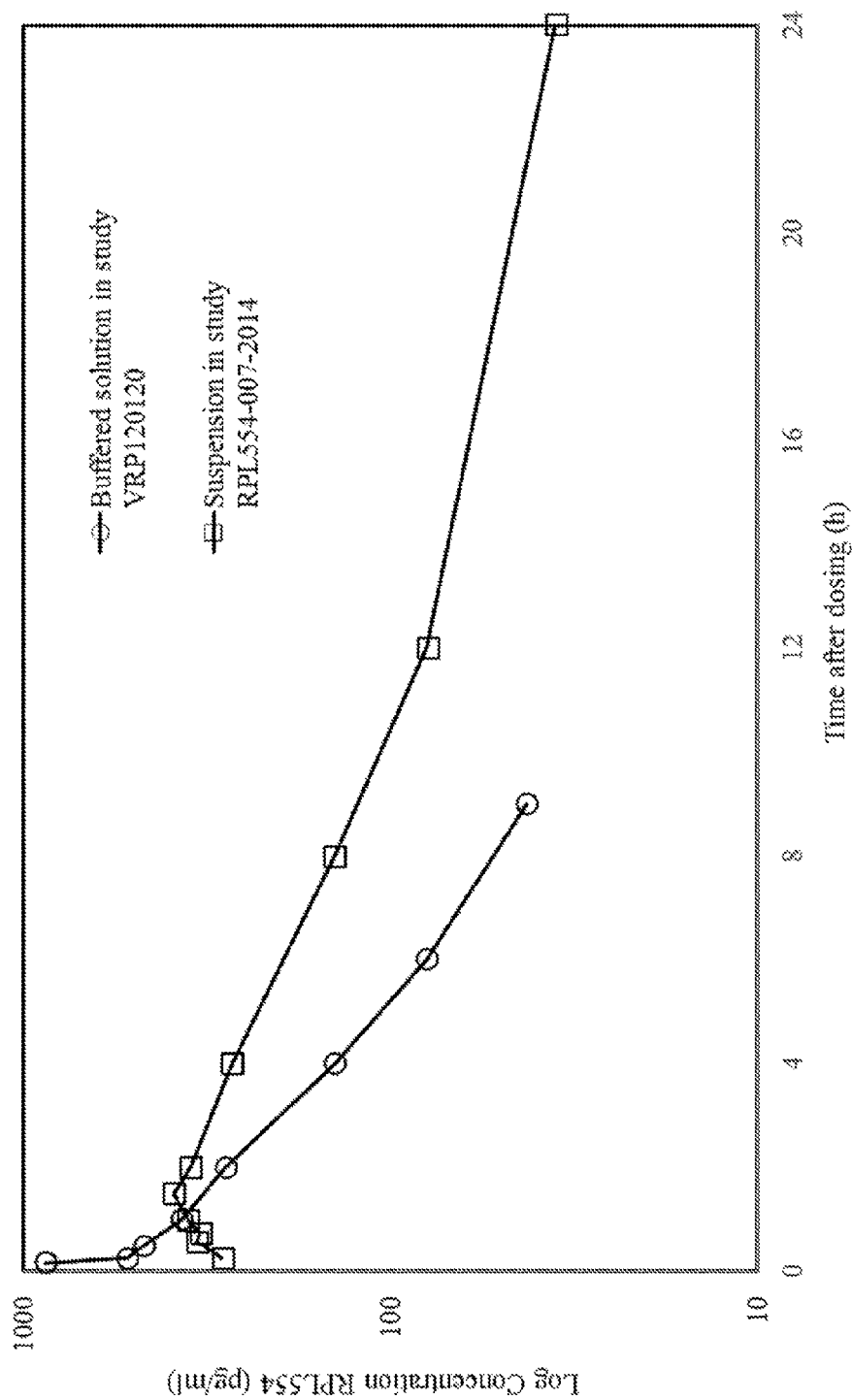

FIG. 3 shows mean concentrations of RPL554 in plasma from healthy human volunteers following administration of either (i) the suspension formulation or (ii) the solution formulation by nebuliser at a nominal dose-level of about 1.5 mg.

DETAILED DESCRIPTION OF THE INVENTION

The particles of RPL554 may be of any suitable size for a use in a liquid pharmaceutical composition suitable for inhalation. Typically, the particles of RPL554 are micronized particles. For instance, the particles of RPL554 may have a Dv50 (median particle size by volume) value of less than or equal to 10 μm or from about 0.1 μm to about 8 μm.

Typically, the particles have a particle size distribution with a Dv50 value of from about 0.2 μm to about 5 μm. More typically, the particles of RPL554 have a particle size distribution with a Dv50 value of from about 0.7 μm to about 3.0 μm. For instance, the particles of RPL554 may have a particle size distribution with a Dv50 value of from 0.9 μm to 1.7 μm, or alternatively from 1.7 μm to 2.7 μm Often, the particles of RPL554 have a particle size distribution with a Dv50 value of from about 1.1 μm to about 2.6 μm.

The Dv50 value is the median particle size for a volume distribution. Thus, half the volume of the particles is comprised in particles having diameters of less than the Dv50 value and half the volume of the particles is comprised in particles having diameters of greater than the Dv50 value. This is a well known manner in which to describe particle size distributions.

The particles typically have a particle size distribution with a Dv10 value of from about 0.4 μm to about 1.0 μm. The particles typically have a particle size distribution with a Dv90 value of from about 2.0 μm to about 4.0 μm. The Dv10 value reflects the particle diameter where 10% of the volume of the sample is in particles having a particle diameter less than the Dv10 value. The Dv90 value reflects the particle diameter where 90% of the volume of the sample is in particles having a particle diameter less than the Dv90 value.

The technique used to measure the Dv50 value is typically laser diffraction. For instance, the RPL554 particles typically have a particle size distribution with a Dv50 value of from about 0.2 μm to about 5 μm as measured by laser diffraction. The particle size distribution analysis can be performed by laser diffraction using the Malvern Spraytec in conjunction with a wet dispersion cell. Typically, the instrument parameters for the Malvern Spraytec are as follows:

particle—standard opaque particle;
refractive index Particle—1.50;
refractive index (imaginary)—0.50;
density of particle—1.00;
refractive index of dispersant—1.33;
controller unit—1000 RPM;
measurement type—timed;
initial sampling time—30 s;
obscuration—20%-30%;
dispersant—1% Polysorbate 20 in deionised water.

The particles of RPL554 may be produced by any pharmaceutically acceptable size reduction process or particle size controlled production process. For instance, the particles may be produced by spray-drying a solution of RPL554, or by controlled crystallisation, or by size reduction of a solid form of RPL554, for example by air jet milling, mechanical micronisation or media milling.

The concentration of particles of RPL554 in the liquid pharmaceutical composition is typically from about 0.01 mg/mL to about 40 mg/mL. More typically, the concentration of particles of RPL554 in the liquid pharmaceutical composition is from about 0.1 mg/mL to about 20 mg/mL. For instance, the concentration of particles of RPL554 in the liquid pharmaceutical composition may be from about 0.01 mg/mL to about 5 mg/mL, or from 0.1 mg/mL to 5 mg/mL. The concentration of particles of RPL554 in the liquid pharmaceutical composition may for instance be from 0.1 mg/mL to 6 mg/mL.

Preferably, the pH of the suspension is from about 6 to about 8, more preferably from about 6.5 to about 7.

The liquid pharmaceutical composition may further comprise one or more surfactants. The surfactants are pharmaceutically acceptable surfactants. The surfactants may be non-ionic surfactants, anionic surfactants, cationic surfactants or zwitterionic surfactants. Preferably, the one or more surfactants are selected from one or more non-ionic surfactants.

The one or more surfactants are typically selected from polyoxyethylene glycol alkyl ethers, polyoxypropylene glycol alkyl ethers, glucoside alkyl ethers, polyoxyethylene glycol octylphenol ethers, polyoxyethylene glycol alkylphenol ethers, glycerol alkyl esters, polyoxyethylene glycol sorbitan alkyl esters (polysorbates), sorbitan alkyl esters, cocamide MEA, cocamide DEA, dodecyldimethylamine oxide, block copolymers of polyethylene glycol and polypropylene glycol (poloxamers) and polyethoxylated tallow amine (POEA).

Preferably, the one or more surfactants are selected from polyoxyethylene glycol sorbitan alkyl esters, for instance polysorbate 20 (polyoxyethylene (20) sorbitan monolaurate), polysorbate 40 (polyoxyethylene (20) sorbitan monopalmitate), polysorbate 60 (polyoxyethylene (20) sorbitan monostearate) and polysorbate 80 (polyoxyethylene (20) sorbitan monooleate), and sorbitan alkyl esters, for instance sorbitan monolaurate, sorbitan monopalmitate, sorbitan monostearate, sorbitan tristearate and sorbitan monooleate.

The total concentration of the one or more surfactants is typically from about 0.01 mg/mL to about 2 mg/mL. The composition often comprises two or more surfactants, for instance a polysorbate and a Span surfactant.

Typically, the liquid pharmaceutical composition further comprises one or more buffers. The buffers are pharmaceutically acceptable buffers. The buffers may be any buffers suitable for use in a liquid pharmaceutical composition suitable for inhalation. The one or more buffers are typically selected from citrate or phosphate buffers. Citrate buffers include citric acid, sodium citrate and mixtures thereof. Phosphate buffers include phosphoric acid, monosodium phosphate, dibasic sodium phosphate and mixtures thereof.

The total concentration of the one or more buffers is typically from about 5 mg/mL to about 40 mg/mL. The composition often comprises two or more buffer components, for instance two phosphate salts, for instance sodium phosphate salts.

A liquid pharmaceutical composition according to the invention may comprise: (a) the particles of RLP554 at a concentration of from about 0.01 mg/mL to about 40 mg/mL; (b) one or more surfactants at a concentration of from about 0.01 mg/mL to about 5 mg/mL; and (c) a buffer at a concentration of from about 5 mg/mL to about 25 mg/mL.

The liquid pharmaceutical composition typically further comprises a tonicity adjuster. The tonicity adjuster may be any pharmaceutically acceptable tonicity adjuster. Examples of tonicity adjusters include simple non toxic salts such as alkali metal halides, for instance sodium chloride and potassium iodide. Typically, the tonicity adjuster is sodium chloride. The concentration of the tonicity adjuster will depend on the amount required to reach the desired tonicity, for instance isotonicity with the body or lungs. The concentration of the tonicity adjuster is typically from about 2 mg/mL to about 8 mg/mL, and more typically from about 3.5 mg/mL to 6 mg/mL.

The liquid pharmaceutical composition may comprise other components. Alternatively, other components may be excluded. In some cases, the liquid pharmaceutical composition does not comprise a $\beta_2$-adrenergic receptor agonist or a muscarinic receptor antagonist (or does not comprise greater than 0.1 wt % total of a $\beta_2$-adrenergic receptor agonist and a muscarinic receptor antagonist).

The diluent may be any pharmaceutically acceptable diluent. The diluent is suitable for administration by inhalation. Examples of suitable diluents include water, ethanol and glycerol. The diluent is preferably water. The diluent is preferably sterile.

A liquid pharmaceutical composition according to the invention typically comprises:
(a) the particles of RLP554 at a concentration of 0.01 mg/mL to 40 mg/mL;
(b) a polyoxyethylene glycol sorbitan alkyl ester at a concentration of from 0.1 mg/mL to 2 mg/mL;
(c) a sorbitan alkyl ester at a concentration of from 0.01 mg/mL to 0.1 mg/mL;
(d) a first phosphate buffer component at a concentration of from 5 mg/mL to 10 mg/mL;
(e) a second phosphate buffer component at a concentration of from 5 mg/mL to 10 mg/mL; and
(f) a tonicity adjuster at a concentration of from 2 mg/mL to 8 mg/mL.

For instance, the liquid pharmaceutical composition may comprise:
(a) the particles of RLP554 at a concentration of 0.05 mg/mL to 25 mg/mL;
(b) polyoxyethylene (20) sorbitan monolaurate (Polysorbate 20, Tween 20) at a concentration of from 0.1 mg/mL to 2 mg/mL;
(c) sorbitan monolaurate (Span 20) at a concentration of from 0.01 mg/mL to 0.1 mg/mL;
(d) monosodium phosphate monohydrate at a concentration of from 5 mg/mL to 10 mg/mL;
(e) dibasic sodium phosphate anhydrous at a concentration of from 5 mg/mL to 10 mg/mL; and
(f) sodium chloride at a concentration of from 2 mg/mL to 8 mg/mL.

Typically, the liquid pharmaceutical composition is suitable for administration by nebulizer.

The invention also provides a nebulizer comprising a liquid pharmaceutical composition according to the invention. The nebulizer is typically loaded with the liquid pharmaceutical composition. The nebulizer typically comprises from about 1 mL to about 200 mL, more typically from 1 mL to 20 mL of the liquid pharmaceutical composition.

Nebulizers use compressed air to aerosolise a liquid pharmaceutical composition into an aerosol that is inhaled into a subject's respiratory tract. Examples of nebulizers include a soft mist nebulizer, a vibrating mesh nebulizer, a jet nebulizer and an ultrasonic wave nebulizer. Suitable nebulizer devices include the Philips I-Neb™ (Philips), the Pari LC Sprint (Pari GmbH), the AERx® Pulmonary Delivery System (Aradigm Corp.) and the Pari LC Plus Reusable Nebulizer (Pari GmbH).

The invention also provides a liquid pharmaceutical composition for use in the treatment of the human or animal body. The composition is as defined herein. The liquid pharmaceutical composition is typically for use in the treatment of the human or animal body, wherein treatment comprises administration by inhalation.

The compositions of the invention allow for delayed release of RPL554 into the bloodstream. The plasma concentration of RPL554 after a certain time is therefore increased relative to the use of known compositions of RPL554. Typically, the blood plasma concentration of RPL554 is greater than or equal to 1 ng/mL at a time greater than or equal to four hours after a nebulised dose of the composition is administered. The nebulised dose is typically from 0.02 mg/kg to 0.6 mg/kg. For example, the nebulised dose may be from 0.2 mg/kg to 0.6 mg/kg. For instance, the invention provides a liquid pharmaceutical composition as defined herein for use in the treatment of the human or animal body, wherein the blood plasma concentration of RPL554 is greater than or equal to 1 ng/mL at a time greater than or equal to four hours after a nebulised dose of from 0.2 mg/kg to 0.6 mg/kg is administered via inhalation of the nebulised composition of the invention. The blood plasma concentration of RPL554 is typically greater than or equal to 1 ng/mL at a time greater than or equal to three, four or five hours after a nebulised dose of the composition is administered.

The invention also provides a method of treating or preventing a disease or condition as defined herein in a subject, which method comprises administering to said subject an effective amount of a liquid pharmaceutical composition as defined herein. Typically, the method is for treating a disease or condition. The disease or condition is typically selected from asthma, allergic asthma, hay fever, allergic rhinitis, bronchitis, emphysema, bronchiectasis, chronic obstructive pulmonary disease (COPD), adult respiratory distress syndrome (ARDS), steroid resistant asthma, severe asthma, paediatric asthma, cystic fibrosis, lung fibrosis, pulmonary fibrosis, interstitial lung disease, skin disorders, atopic dermatitis, psoriasis, ocular inflammation, cerebral ischaemia and auto-immune diseases. Preferably the method comprises treating asthma or chronic obstructive pulmonary disease (COPD), more preferably COPD.

An effective amount of RPL554 is typically from about 0.01 mg/kg to 50 mg/kg for a single dose. An effective amount of RPL554 is often from about 0.01 mg/kg to 1 mg/kg for a single dose. For instance, an effective amount may be a dose of from about 0.1 mg to about 500 mg, or from about 0.1 mg to 100 mg, preferably from about 0.1 mg to about 6 mg. An effective amount may be from 0.1 mg to 12 mg. A single dose of RPL554 may be from 0.5 mg to 3 mg, for instance about 1.5 mg. Doses may be administered daily. For instance, the dose of RPL554 may be from 0.01 mg/kg/day to 50 mg/kg/day, typically from 0.01 mg/kg/day to 10 mg/kg/day or from 0.01 mg/kg/day to 1 mg/kg/day. These doses are typically the nominal dose emitted from the inhaler. The liquid pharmaceutical composition may be administered once, twice or three times a day, or may be administered twice, three times, four times or five times a week. The composition may be administered as often as required by the patient.

An effective amount may be a dose of from about 0.1 mg to about 500 mg, or from about 0.1 mg to 100 mg, preferably from about 0.5 mg to about 6 mg. An effective amount may be from 0.1 mg to 12 mg. A single dose of RPL554 may be from 0.5 mg to 24 mg, which may be administered by nebuliser. A single dose of RPL554 may be from 0.5 mg to 6 mg, for instance about 1.5 mg. Doses may be administered once, twice or three times daily. For instance, the dose of RPL554 may be from 0.1 mg/day to 50 mg/day, typically from 1.5 mg/day to 18 mg/day. These doses are typically the nominal dose emitted from the inhaler. The liquid pharmaceutical composition may be administered once, twice or three times a day, or may be administered twice, three times, four times or five times a week. The composition may be administered as often as required by the patient.

It is a surprising finding of the present invention that a suspension formulation of RPL554 allows for high doses of RPL554 to be administered to a patient without a concomitant increase in cardiovascular liability. The liquid pharmaceutical composition is therefore suitable for use in the treatment of patients suffering from cardiovascular disorders or at risk from suffering cardiovascular disorders.

For example, the composition may be used to treat a disease or condition as defined above in a patient suffering from cardiovascular vulnerability. Patients suffering from cardiovascular vulnerability are typically those at increased risk of adverse events arising from tachycardia or hypertension. More typically, patients suffering from cardiovascular vulnerability are those suffering from a pre-existing heart condition, or a condition which would be aggravated by tachycardia or hypertension. Such patients include those suffering from coronary artery disease, cardiomyopathy, hypertension, hypertensive heart disease, heart failure, arrhythmia, cardiac dysrhythmias, endocarditis, myocarditis, valvular heart disease and stroke. Also included are patients who have suffered a heart attack.

The invention is described in more detail by the following Examples.

EXAMPLES

Example 1

Formulation and Stability of RPL554 Suspension Formulation

Liquid pharmaceutical compositions according to the invention were produced with the formulations set out Tables 1 and 2 below.

TABLE 1 formulation of variant 1a (0.4 mg/mL)

| Constituent | Function | Concentration (mg/mL) |
| --- | --- | --- |
| RPL554 (micronized) | Active compound | 0.4 |
| Polysorbate 20 (Tween 20) | Surfactant | 0.50 |
| Sorbitan Monolaurate (Span 20) | Surfactant | 0.05 |
| Monosodium Phosphate Monohydrate | Buffer | 6.58 |
| Dibasic Sodium Phosphate Anhydrous | Buffer | 6.80 |
| Sodium Chloride | Tonicity Adjuster | 4.80 |
| Water | Diluent | Q.S. |

TABLE 2 formulation of variant 1b (20.0 mg/mL)

| Constituent | Function | Concentration (mg/mL) |
| --- | --- | --- |
| RPL554 (micronized) | Active compound | 20.0 |
| Polysorbate 20 (Tween 20) | Surfactant | 0.50 |
| Sorbitan Monolaurate (Span 20) | Surfactant | 0.05 |
| Monosodium Phosphate Monohydrate | Buffer | 6.58 |
| Dibasic Sodium Phosphate Anhydrous | Buffer | 6.80 |
| Sodium Chloride | Tonicity Adjuster | 4.80 |
| Water | Diluent | Q.S. |

Assay testing was performed in duplicate. The key method parameters are as follows:

mobile phase: acetonitrile:water:TFA (45:55:0.1);

column: Waters X-Bridge phenyl, 3.5 μm, 150×4.6 mm;

flow rate: 1.5 ml/min;

injection volume: 10 μL;

detection: UV @ 254 nm;

runtime: 6 minutes; and sample and standard concentration: 0.1 mg/mL.

Variant 1a was stored under conditions of either (i) a temperature of 25° C. and a relative humidity (RH) of 60% or (ii) a temperature of 40° C. and a RH of 75%. The appearance, pH, assay, impurities and particle size distribution (PSD) were measured initially, at 1 month, at 2 months and at 6 months (6 months only for the 25° C. and RH of 60% conditions). The amount of impurities were measured by HPLC with the relative retention time (RRT) of the impurity indicated.

The results are shown in Tables 3 and 4 below.

TABLE 3

| Stability of variant 1a under conditions: 25° C./60% RH | | | | |
|---|---|---|---|---|
| Test | Initial | 1 month | 2 months | 6 months |
| Appearance | Light yellow suspension free from agglomerates | Light yellow suspension free from agglomerates | Light yellow suspension free from agglomerates | Light yellow suspension free from agglomerates |
| pH | 6.55 | 6.59 | 6.68 | 6.51 |
| Assay (mg/g) | 0.372 | 0.374 | 0.373 | 0.372 |
| Impurities (% area) | | | | |
| Total | 1.8 | 1.8 | 1.6 | 1.9 |
| Greatest | 0.490 (RRT 0.28) | 0.533 (RRT 0.26) | 0.429 (RRT 0.26) | 0.463 (RRT 0.26) |
| Second greatest | 0.401 (RRT 1.13) | 0.408 (RRT 1.12) | 0.389 (RRT 1.12) | 0.432 (RRT 1.12) |
| PSD (Dv50, μm) | 2.282 | 2.069 | 2.089 | 2.133 |

TABLE 4

| Stability of variant 1a under conditions: 40° C./75% RH | | | |
|---|---|---|---|
| Test | Initial | 1 month | 2 months |
| Appearance | Light yellow suspension free from agglomerates | Light yellow suspension free from agglomerates | Light yellow suspension free from agglomerates |
| pH | 6.55 | 6.91 | 6.67 |
| Assay (mg/g) | 0.372 | 0.374 | 0.377 |
| Impurities (% area) | | | |
| Total | 1.8 | 1.7 | 1.6 |
| Greatest | 0.490 (RRT 0.28) | 0.445 (RRT 0.26) | 0.428 (RRT 0.26) |
| Second greatest | 0.401 (RRT 1.13) | 0.409 (RRT 1.12) | 0.380 (RRT 1.12) |
| PSD (Dv50, μm) | 2.28 | 2.10 | 2.14 |

Variant 1b was stored under conditions of either (i) a temperature of 25° C. and a relative humidity (RH) of 60% or (ii) a temperature of 40° C. and a RH of 75%. The appearance, pH, impurities and particle size distribution (PSD) were measured initially, at 1 month, and at 2 months. The amount of impurities were measured by HPLC with the relative retention time (RRT) of the impurity indicated.

The results are shown in Tables 5 and 6 below.

TABLE 5

| Stability of variant 1b under conditions: 25° C./60% RH | | | |
|---|---|---|---|
| Test | Initial | 1 month | 2 months |
| Appearance | Yellow suspension free from agglomerates | Yellow suspension free from agglomerates | Yellow suspension free from agglomerates |
| pH | 6.55 | 6.67 | 6.68 |
| Assay (mg/g) | 18.72 | 18.86 | 18.54 |
| Impurities (% area) | | | |
| Total | 1.2 | 1.2 | 1.2 |
| Greatest | 0.399 (RRT 1.13) | 0.401 (RRT 1.12) | 0.401 (RRT 1.12) |
| Second greatest | 0.306 (RRT 1.11) | 0.328 (RRT 1.11) | 0.329 (RRT 1.11) |
| PSD (Dv50, μm) | 2.11 | 2.37 | 2.05 |

TABLE 6

| Stability of variant 1b under conditions: 40° C./75% RH | | | |
|---|---|---|---|
| Test | Initial | 1 month | 2 months |
| Appearance | Yellow suspension free from agglomerates | Yellow suspension free from agglomerates | Yellow suspension free from agglomerates |
| pH | 6.55 | 6.76 | 6.3 |
| Assay (mg/g) | 18.72 | 18.99 | 19.01 |
| Impurities (% area) | | | |
| Total | 1.2 | 1.2 | 1.2 |
| Greatest | 0.399 (RRT 1.13) | 0.394 (RRT 1.12) | 0.388 (RRT 1.13) |
| Second greatest | 0.306 (RRT 1.11) | 0.308 (RRT 1.11) | 0.322 (RRT 1.11) |
| PSD (Dv50, μm) | 2.11 | 2.09 | 2.13 |

As can be seen from Tables 3 to 6, the liquid pharmaceutical composition according to the invention shows excellent long term stability with no significant variation in pH or the amount of impurities present. This stability is even observed after 2 months at 40° C.

Comparative Example 1

Formulation and Stability of RPL554 Solution Formulation

A similar stability test was performed for the solution formulation of RPL554. A 1.0 mg/ml solution of RPL554 in an aqueous citrate/phosphate buffer solution at a pH of approximately 3.2 was held under conditions of a temperature of 25° C. and a relative humidity (RH) of 60% for six months. The appearance, pH, assay and impurities present were measured initially and at 6 months. The results are shown in Table 7 below.

TABLE 7

Stability of RPL554 solution under conditions: 25° C./60% RH

| Test | Initial | 6 months |
|---|---|---|
| Appearance | A clear, slightly coloured solution. Free from visible contamination | A clear, slightly coloured solution. Free from visible contamination. |
| pH | 3.04 | 3.00 |
| Assay | 0.98 mg/mL | 0.98 mg/mL |
| Impurities by HPLC | | |
| RRT 0.85 | 0.19% | 0.19% |
| RRT 0.87 | 0.15% | 0.42% |
| RRT 1.03 | <0.10% | <0.10% |
| RRT 1.09 | 0.20% | 0.16% |
| RRT 1.12 | 0.54% | 0.57% |
| RRT 1.14 | 0.14% | <0.10% |
| RRT 1.15 | 0.11% | <0.10% |

While there is no change in the appearance of the solution, there is a significant increase in the amount of the impurity with the RRT value of 0.87. This impurity has been identified as a hydrolysis product of RPL554. The solution of RPL554 is less stable than the suspension formulation according to the invention.

Example 2

Particle Size Distribution

The particle size distribution of a sample of micronized RPL554 suitable for use in nebulized formulations was evaluated using laser diffraction. The particle size distribution analysis was performed by laser diffraction using the Malvern Spraytec in conjunction with a wet dispersion cell.

The results are as follows: Dv10=0.69 μm; Dv50=1.35 μm; Dv90=2.5 μm.

Example 3

Formulations

RPL554 suspension and solution formulations were prepared as follows. These formulations were used in Examples 4 to 6.

Formulation constituents (Suspension)

| 20 mg/ml RPL554 Suspension Constituent | Amount | Concentration (mg/mL) |
|---|---|---|
| RPL554 - Micronised | 2.12 g[a] | 20 mg/mL |
| Wetting Solution | 10.0 mL | N/A |
| Buffer Solution | To 100 mL | N/A |

[a]Includes a 6% overage for expected manufacturing losses
Vehicle = as above, omitting RPL554

| RPL554 Buffer Solution Constituent | Amount (g) | Concentration (mg/mL) |
|---|---|---|
| Monosodium phosphate monohydrate | 32.9 | 6.58 |
| Dibasic sodium phosphate anhydrous | 34.0 | 6.80 |
| Sodium chloride | 24.0 | 4.80 |
| Water for Injection | To 5000 ml | N/A |

| RPL554 Wetting Solution Constituent | Amount (g) | Concentration (mg/mL) |
|---|---|---|
| Polysorbate 20 (Tween 20) | 10.0 | 5.00 |
| Sorbitan monolaurate (Span 20) | 1.0 | 0.50 |
| RPL554 Buffer Solution | To 2000 mL | N/A |

Method of preparation (Suspension)

RPL554 Buffer Solution: The required amount of vehicle excipients were weighed out into a suitable container and made up to the required volume with water for injection. The excipients were magnetically stirred for 10 minutes until the buffer salts were fully dissolved. The pH was measured, recorded and adjusted if necessary to pH 7.0 ± 0.3 using HCl/NaOH and filtered through a 0.22 μm filter.

RPL554 Wetting Solution: The required amount of polysorbate 20 was weighed into a suitable container and the required amount of sorbitan monolaurate was added. The wetting solution was magnetically stirred for 10 minutes, then transferred to a larger container with buffer solution and made up to the final volume with the buffer solution. The solution was magnetically stirred for 10 minutes and filtered through a 0.22 μm filter.

Vehicle: The required volume of RPL554 Wetting Solution was measured into a suitable container and made to the final volume with RPL554 Buffer Solution, mixed with a magnetic stirrer for 10 minutes. The pH was measured, recorded and adjusted if necessary to pH 7.0 ± 0.3 using HCl/NaOH.

20 mg/mL RPL554 Suspension: The required amount of RPL554 was weighed into a small beaker and the required amount of Wetting Solution was added. The suspension was mixed using a Silverson mixer fitted with a ⅝" high sheer screen for approximately 1 minute at 8000 rpm. The mixture was transferred to a new clean, dry beaker rinsing with Buffer Solution. The required weight was made up with Buffer Solution and mixed using a Silverson mixer fitted with a 1" high sheer screen for approximately 1 minute at 8000 rpm. The pH was measured, recorded and adjusted if necessary to pH 7.0 ± 0.3 using HCl/NaOH. The solution was transferred into the final container.

For the lower concentrations of RPL554 suspensions, the required amount of 20 mg/mL formulation was weighed out and diluted to the required volume with vehicle using a syringe fitted with a 0.22 μm filter. The formulation was gently mixed on a magnetic stirrer for 5 minutes.

Formulation constituents (Solution)

| 1 mg/mL (pH 3.5) RPL554 Solution Constituent | Amount |
|---|---|
| RPL554 | 100 mg |
| 0.1M Citric acid solution | 22.5 mL |
| 0.2M Dibasic sodium phosphate dodecahydrate solution | 9.7 mL |
| 0.9% (w/w) Saline solution | 67.8 mL |

| 1.5 mg/mL (pH 2.5) RPL554 Solution Constituent | Amount |
|---|---|
| RPL554 | 150 mg |
| 0.1M Citric acid solution | 45 mL |
| 0.2M Dibasic sodium phosphate dodecahydrate solution | 5 mL |
| 0.9% (w/w) Saline solution | 50 mL |

Vehicle: As above, omitting RPL554

Method of preparation (Solution)

RPL554 0.1M Citric Acid Solution: The required amount of citric acid was weighed into a suitable container, made up to the required volume with 0.9% saline and magnetically stirred until fully dissolved.

RPL554 0.2M Dibasic Sodium Phosphate Solution: The required amount of dibasic sodium phosphate anhydrous was weighed into a suitable container, made up to the required volume with 0.9% saline and magnetically stirred until fully dissolved.

-continued

Vehicle: The required volume of Citric Acid Solution, Dibasic Sodium Phosphate Solution and 0.9% saline were measured into a suitable container and mixed thoroughly. The pH was measured and adjusted if necessary (pH 3.5 (±0.3) or pH 2.5 (±0.2)) by drop wise addition of further citric acid or sodium phosphate solution as required.
RPL554 Solution: The required amount of test material was weighed into a suitable container, made up to the final volume with Vehicle and magnetically stirred until fully dissolved. The pH was measured and adjusted if necessary.

Example 4

Toxicokinetic Profile in Rats

Summary

Han Wistar rats (5/sex/group) were dosed by nose-only inhalation once daily at target doses of 2.4, 8.4 or 21.6 mg/kg/day of an RPL554 suspension according to the invention for 7 consecutive days (groups 2, 3 and 4). An additional 5 rats/sex/group received the vehicle suspension and acted as controls (group 1). The duration of dose administration was 240 minutes on each day. At the end of the treatment period, all surviving animals were euthanized and necropsied. Satellite animals (3/sex/group) were similarly dosed and bled on Day 7 for toxicokinetic analysis. An additional group of satellite animals (3/sex) were dosed by nose-only inhalation once daily at a target dose of 2.4 mg/kg/day RPL554 solution for comparison with the RPL554 suspension and bled on Day 7 for toxicokinetic analysis (group 5). Mean aerosol concentrations and achieved doses are presented in Table 8 below.

TABLE 8

Mean Aerosol Concentrations and Achieved Doses

| Group | Type of Formulation | Target exposure level (µg/L) | Achieved exposure level (µg/L) | Target dose (mg/kg/day) | Achieved dose (mg/kg/day) | Formulation concentration (mg/mL) |
| --- | --- | --- | --- | --- | --- | --- |
| 1 | Vehicle | 0 | 0.00 | 0 | 0 | 0 |
| 2 | Suspension | 13 | 18.10 | 2.4 | 3.27 | 1.5 |
| 3 | Suspension | 47 | 55.18 | 8.4 | 9.96 | 4.5 |
| 4 | Suspension | 121 | 141.51 | 21.6 | 25.49 | 12 |
| 5 | Solution | 13 | 14.47 | 2.4 | 2.62 | 1.6 |

Toxicokinetic Results

The toxicokinetic profile of the RPL554 suspension was measured at different doses (groups 2, 3 and 4). This was compared with the toxicokinetic profile of the known RPL554 solution (group 5). The dosages administered to group 2 and group 5 are similar. Group 1 is the control group.

The toxicokinetic parameters of RPL554 in suspension (invention) or solution (comparative) form were evaluated on day 7 of 1 week of daily inhalation exposure of the RPL554 compositions to rats. The results are shown in Tables 10 and 11 below. The parameters measured are maximum concentration of RPL554 in the blood plasma of the rats ($C_{max}$), the time taken to reach Cmax ($T_{max}$) and the area under the dose curve after 8 hours ($AUC_{8h}$).

TABLE 10 toxicokinetic results for male rats

| Group | Achieved dose (mg/kg/day) | $C_{max}$ (ng/mL) | $T_{max}$ (hours, median) | $AUC_{8h}$ (ng · h/mL) |
| --- | --- | --- | --- | --- |
| 1 (vehicle) | 0 | 0 | 0 | 0 |
| 2 (suspension) | 3.27 | 10.5 | 4.25 | 41.9 |
| 3 (suspension) | 9.96 | 44.1 | 4.25 | 172 |
| 4 (suspension) | 25.49 | 94.1 | 4.083 | 372 |
| 5 (solution) | 2.62 | 53.4 | 4.083 | 139 |

TABLE 11 toxicokinetic results for female rats

| Group | Achieved dose (mg/kg/day) | $C_{max}$ (ng/mL) | $T_{max}$ (hours, median) | $AUC_{8h}$ (ng · h/mL) |
| --- | --- | --- | --- | --- |
| 1 (vehicle) | 0 | 0 | 0 | 0 |
| 2 (suspension) | 3.27 | 19.9 | 4.25 | 79.1 |
| 3 (suspension) | 9.96 | 133 | 4.25 | 478 |
| 4 (suspension) | 25.49 | 573 | 4.25 | 2030 |
| 5 (solution) | 2.62 | 52.0 | 4.083 | 153 |

These results demonstrate that it is possible to reach substantially higher $C_{max}$ values using the liquid pharmaceutical composition of the invention (e.g groups 3 and 4) compared with a solution composition (group 5). The solubility limited dose feasible from a solution of RPL554 prevents such $C_{max}$ values being achieved with a solution composition. The suspension compositions are also shown to have a delayed release, with greater $T_{max}$ values observed for groups 2 to 4.

Example 5

Toxicokinetic Profile in Dogs

The toxicokinetic profile of RPL554 suspensions according to the invention were evaluated for beagle dogs. The study design was as set out in Table 12 below.

TABLE 12 study design, doses and nominal concentrations

| Phase | Dose | Treatment | Formulation | Target dose of RPL554 (mg/kg/day) | Target aerosol concentration* µg/L | Nominal concentration (mg/mL) |
|---|---|---|---|---|---|---|
| 1 | 1 | RPL554 | Suspension | 1 | 19.8 | 1.5 |
| 1 | 2 | RPL554 | Suspension | 3 | 59.4 | 4.5 |
| 1 | 3 | RPL554 | Suspension | 9 | 178 | 16 |
| 2 |   | RPL554 | Suspension | 9 | 178 | 16 |
| 3 |   | RPL554 | Suspension and solution | 0.5 | 10 | 1.5 (suspension) 1.0 (solution) |

*Aerosol concentration calculated assuming an exposure duration of 120 minutes and a body weight of 12 kg Animals received the test substance, RPL554, by inhalation administration for 3 days at each dose in the variable dose phase (Phase 1), with at least 2 days washout period between doses. In the constant dose phase (Phase 2), animals received the test substance for 7 consecutive days. In the crossover phase (Phase 3), animals received the test substance as a single exposure to the suspension formulation followed by 2 days off-dose followed by a single exposure to the comparative solution formulation.

Toxicokinetic Results

Following 7 days of dosing at 9.82 mg/kg/day with the RPL554 suspension (group 2), the $C_{max}$ values for males and females were 116 ng/mL and 95.9 ng/mL, respectively, and the $AUC_{6h}$ values for the males and females were 389 ng·h/mL and 289 ng·h/mL, respectively.

After a single exposure of RPL554 suspension at 0.395 mg/kg, the $C_{max}$ values for the male and females were 13.4 ng/mL and 12.7 ng/mL, respectively, and the $AUC_{6h}$ values for the male and females were 33.9 ng·h/mL and 31.5 ng·h/mL, respectively.

After a single exposure of RPL554 solution at 0.543 mg/kg, the $C_{max}$ values for the male and females were 40.9 ng/mL and 34.2 ng/mL, respectively, and the $AUC_{6h}$ values for the male and females were 74.6 ng·h/mL and 62.8 ng·h/mL, respectively.

Here it is observed that it is possible to achieve high $C_{max}$ and AUC values using the RPL554 suspension according to the invention (e.g. 116 ng/mL and 95.9 ng/mL).

The toxicokinetic results also confirm that the suspension formulation gives a delayed release compared to the solution formulation. This can be seen from the data from the phase 3 experiment (separate single doses of the suspension formulation). These data are presented in Table 13 below, where the solution formulation (target dose 0.5 mg/kg/day, actual 0.543 mg/kg/day) is compared with the suspension formulation (target dose 0.5 mg/kg/day, actual 0.395 mg/mg/day). Table 13 shows plasma concentrations (ng/mL) over time following treatment with a single dose of the suspension or a single dose of the solution. The two treatments were performed two days apart. Data for all three dogs are presented: one male dog (61) and two female dogs (62 and 64). BLQ refers to plasma concentrations of less than 1.00 ng/mL.

TABLE 13

RPL554 plasma concentration values (ng/mL) for 3 dogs following a dose with an RPL554 suspension and an RPL554 solution

| Time (hours) | Dog 61 (M) Suspension | Dog 61 (M) Solution | Dog 62 (F) Suspension | Dog 62 (F) Solution | Dog 64 (F) Suspension | Dog 64 (F) Solution |
|---|---|---|---|---|---|---|
| 0 | BLQ | BLQ | BLQ | BLQ | BLQ | BLQ |
| 0.017 | 11 | 39.7 | 9.83 | 35.2 | 13.5 | 33.1 |
| 0.25 | 13.4 | 40.9 | 11.6 | 26.5 | 13.7 | 26.5 |
| 0.667 | 10.4 | 13 | 7.26 | 15.7 | 10.8 | 13 |
| 1.667 | 4.57 | 4.84 | 2.51 | 3.31 | 4.99 | 3.15 |
| 3 | 2.88 | 1.23 | 1.87 | 1.99 | 2.42 | 1.21 |
| 4 | 1.81 | BLQ | 1.4 | BLQ | 1.74 | BLQ |

The data in Table 13 demonstrates that the suspension formulation of RPL554 leads to a more delayed release profile than the solution formulation of RPL554. For instance, the plasma concentration of RPL554 is below the detectable limit 4 hours after inhalation of the solution formulation for all dogs, whereas at least 1.4 ng/mL of RPL554 is present after 4 hours in the blood plasma for all dogs following inhalation of the suspension.

Example 6

Lung Function in Guinea Pigs

Introduction

RPL554 causes bronchoprotection against intravenously administered spasmogenic agents when administered as dry power or when prepared as a solution in acidifed (pH 2.5) saline.

This functional antagonism (1.5 doubling dilution ie 2.8 fold) against methacholine has also been verified in human asthmatic subjects (Franciosi et al., 2013). This Example evaluated the bronchoprotection afforded by RPL554 when presented as the new suspension formulation for nebulisation.

Methodology

Drug Exposure

Male Dunkin Hartley guinea-pigs (300-400 g) were placed in a custom built aerosol chamber and exposed to either vehicle (0.9% saline pH 2.5), RPL554 (2.5 mg/mL solution) or RPL554 (1 mg/mL solution) for a 15 min period. Aerosols were generated using an Ultrasonic Nebuliser (Ultraneb 99) and a flow rate of 1 L/min was used to direct the nebulized solution to an aerosol chamber which contained 4 arms that allows animals to be restrained with their upper respiratory tract (ie nose) protruding into the aerosol chamber.

After this 15 min exposure period, animals were allowed to recover and then prior to the 2 h and 5 h post drug exposure, animals were anaesthetised with urethane (1.5 g/kg) and a midline incision made to expose the trachea. A tracheostomy was performed, and a tracheal cannula tied in place and attached to a pneumotachograph which in turn was connected to a Validyne pressure transducer (+2 cmH$_2$O) for the detection of flow. Breath by breath changes in airflow were measured using a Lung Function Recording system (LFR, Version 9, Mumed UK) and displayed in real time on a PC. The flow signal was integrated to give a measure of tidal volume.

A cannula was inserted into the thoracic cavity between the 3rd and 5th intercostal space and connected to the negative side of a Validyne pressure transducer (+20 cmH$_2$O). The positive side of the pressure transducer was connected to the side of the pneumotachograph proximal to the animal, in order to obtain a measure of transpulmonary pressure (TPP: difference between mouth and thoracic pressure). The lung function parameters, total airway resistance (RL; cmH$_2$O.s/L) and dynamic lung compliance (mL/cmH$_2$O) was derived from each measure of flow, tidal volume and TPP by the method of integration. The carotid artery was cannulated for the measurement of blood pressure, respectively. Cumulative concentration-effect curves were established and the provocation concentration (PC) of acetylcholine which cumulatively produced a 50% increase in RL (PC50).

Acetylcholine Exposure

Bronchoconstriction to acetylcholine (0.25 to 16 mg/mL, 4 sec exposure) was monitored 2 h and 5 post administration of a solution of RPL554 (1 and 2.5 mg/mL) or vehicle (acidified saline pH 3.5 or pH 2.5). Aerosols of acetylcholine were generated with an Aeroneb® Lab Nebulizer (Aerogen Inc). The inflow was directed either via the pneumotachograph for the measurement of respiratory lung mechanics, or shunted through the nebulizer for the purposes of delivering drug directly into the lung (respiratory mechanics not measured during the 4 sec exposure period).

In a separate series of experiments, lung function was performed 2 and 5 h post inhalation of the new suspension formulation of RPL554 (2.5 mg/mL and 10 mg/mL) and the vehicle.

Results

Baseline Parameters

Baseline total lung resistance (RL), dynamic lung compliance (Cdyn), mean arterial blood pressure (BP) and nebulizer output were measured in animals previously exposed to vehicle control (saline pH 2.5), and solution formulations of RPL554 (1 mg/mL or 2.5 mg/mL, FIG. 1) and to new suspension formulations of RPL554 (2.5 mg/mL and 10 mg/mL, FIG. 2). Baseline respiratory and cardiovascular parameters were made prior to acetylcholine exposure and were monitored 2 and 5 h post saline or RPL554 exposure in anaesthetised guinea-pigs.

Lung Function Parameters

In general RL represents changes in airway diameter in the central airways following the activation of muscarinic receptors on airway smooth muscles in this region of the lung. Acetylcholine was chosen for its short duration of action.

1. RPL554 Solution Formulation

Acetylcholine administered to anaesthetized guinea-pigs by the inhaled route caused a dose dependent bronchoconstrictor response as determined by changes in RL measured 2 h and 5 h post saline and RPL554 (1 mg/mL, 2.5 mg/mL solution) exposure.

1.1—Analysis of Acetylcholine RL PC50

Post hoc analysis of the arithmetic mean demonstrated a significant bronchoprotection at the 2 h point for RPL554 1 mg/mL solution (mean diff=3.5 (0.11-8.83) mg/mL, P=0.0445) and 2.5 mg/mL at the 2 h (4.7 (0.4-9) mg/mL, P=0.0357) and 5 h time point (3.4 (0.9-6) mg/mL, P=0.0133). The degree of bronchoprotection was less evident at 5 h for 1 mg/mL RPL554 solution (2.5 (−0.17-5.2) mg/mL, P=0.0628).

Figure 1:
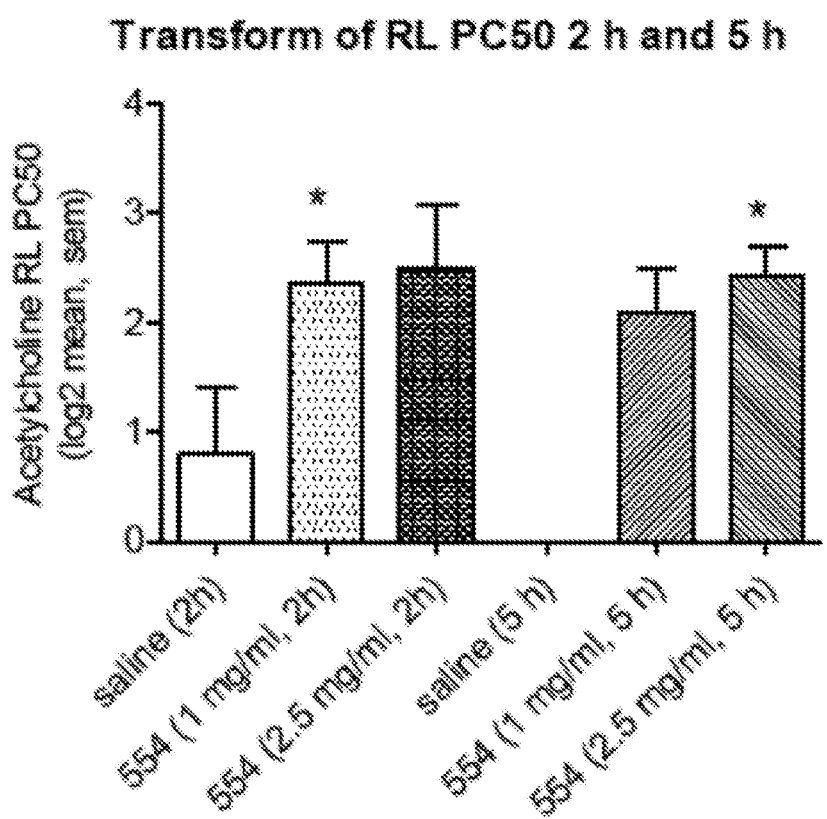
FIG. 1—The provocation concentration (PC) of acetylcholine which cumulatively produced a 50% increase in total airway resistance (Acetylcholine RL PC50) in animals treated with saline or RPL554 solution formulation: 2 and 5 h time point: Acetylcholine RL PC50 was log transformed for the purposes of statistical analysis. Post hoc t-test of the untransformed data showed differences between groups vs saline. *Non parametric analysis did show a significant difference between 2 h (1 mg/mL RPL554 solution, P=0.0190 unadjusted) and 5 h (2.5 mg/mL solution, P=0.0095 unadjusted) vs saline group. N values=6, 4, 4; 4, 4 left to right. (Note 5 h control not plotted).

A significant difference between 2 h (1 mg/mL RPL554, P=0.0190 unadjusted) and 5 h (2.5 mg/mL, P=0.0095 unadjusted) RPL554 solution vs saline group was observed (FIG. 1).

2. New Suspension Formulation of RPL554

Acetylcholine administered to anaesthetized guinea-pigs by the inhaled route caused a dose dependent bronchoconstriction as determined by changes in RL measured 2 h and 5 h post saline and RPL554 suspension (2.5 mg/mL and 10 mg/mL) exposure. Dose dependent reduction in baseline lung compliance (Cdyn) was also simultaneously recorded following increasing concentrations of acetylcholine 2 h and 5 h post saline or RPL554 suspension (2.5 mg/mL and 10 mg/mL) exposure.

2.1—Analysis of Acetylcholine RL PC50

Analysis of variance of the log 2 transformed data for Acetylcholine RL PC50 revealed an overall drug effect at the 2 h (P=0.0238). For the 2 h time group, this was reflected by a significant difference between the 10 mg/mL RPL554 suspension and vehicle group (Mean fold difference=2.67 (1.12-6.36), P<0.05). Despite the greater mean difference, between RPL554 (10 mg/mL suspension) versus vehicle at the 5 h time point 14 fold shift (0.5-400), the wide confidence interval is the reason why statistical difference was not achieved (FIG. 2, upper panel).

The vehicle data for the 2 and 5 h time points were combined and re-analyzed (FIG. 2 lower panel). There was an overall significant treatment effect (P=0.0016) which was reflected by a significant degree of bronchoprotection with 2.5 mg/mL RPL554 suspension (2.52 fold (1-5.72), P<0.05 and 10 mg/mL RPL554 (4.67 fold (2-11), P<0.05). At the 5 h time point, RPL554 10 mg/mL suspension caused a significant degree of bronchoprotection (2.77 fold (1.3-6.0) (FIG. 2, lower panel).

Summary

RPL554 inhibited bronchoconstriction induced by aerosolized administered acetylcholine when measured 2 and 5 h post drug exposure. Both the RPL554 solution formulations (1 mg/mL, 2.5 mg/mL) and the new RPL554 suspension formulations (2.5 mg/mL, 10 mg/mL) produced a statistically significant bronchoprotection.

Example 7

Pharmacokinetic Study in Humans

A phase I, randomised, double-blind, placebo-controlled, study was performed to assess the safety, tolerability and pharmacokinetics of single inhaled doses of RPL554 suspension formulation according to the invention, administered by nebuliser to healthy male subjects aged 18 to 50 inclusive.

The nominal dose of suspension formulation was approximately 1.5 mg, being essentially equivalent to the 0.018 mg/kg dose previously shown to be well-tolerated in clinical studies with the solution formulation.

The suspension formulation used was a sterile suspension for nebulisation containing 1.5 mg micronised RPL554 drug substance in 5 mL phosphate buffered saline solution at pH 7, with surfactants (Tween 20 and Span 20) (as described in Example 1 above, but with a different concentration of RPL554). The dosing of the suspension was performed using a standard Jet nebuliser (PARI LC Sprint).

Blood samples (4 mL at each time point) were collected at appropriate time intervals after administration. Samples were collected by venepuncture or via indwelling cannula in the forearm into lithium heparin tubes and will be immediately chilled (ice bath). The blood was centrifuged within 15 minutes of collection. The plasma was separated in a refrigerated centrifuge (about 4° C.) at 1100 g for 15 minutes and transferred into polypropylene tubes. The concentration of the active was then measured.

The mean results are presented in FIG. 3, which shows the mean concentration curves for the subjects after administration of the solution or suspension formulations. The results for the solution formulation were derived from a previous clinical study (The Lancet Respiratory Medicine Volume 1, No. 9, p. 714-727, November 2013) which used a sterile solution for nebulisation containing RPL554 dissolved in citrate-phosphate buffered saline at pH 3.2. The quantity administered via nebuliser was such that the nominal RPL554 dose was 0.018 mg/kg (~1.26 mg for a 70 kg person).

Mean pharmacokinetic parameters measured during the study are presented in Table 14 below.

TABLE 14

| Formulation | $C_{max}$ (pg/ml) | $AUC_{inf}$ (pg · h/ml) | Half-life (h) |
|---|---|---|---|
| Solution | 870 | 1833 | 3 |
| Suspension | 393 | 3795 | 10 |

The values in Table 14 demonstrate that the suspension formulation according to the invention has a substantially improved pharmacokinetic profile compared with the comparative solution formulation. In particular, the area under the curve (AUC) and the half-life are both significantly increased. This demonstrates that the suspension formulation provides an unexpectedly improved way by which RPL554 may be administered by inhalation.

Example 8

Twelve Months Stability Study

Three batches of the suspension formulation of the invention were made with the compositions set out in Table 15 below.

TABLE 15

| Constituent | Concentration (mg/mL) |
|---|---|
| RPL554 (heat treated API) | 0.5, 2.5 and 10 |
| Polysorbate 20 (Tween 20) | 0.5 |
| Sorbitan monolaurate (Span 20) | 0.05 |
| Monosodium phosphate monohydrate | 6.58 |
| Dibasic sodium phosphate anhydrous | 6.80 |
| Sodium chloride | 4.80 |
| Water for injection | To weight |

Analytical Testing

Analytical testing was performed after 1, 3, 6 and 12 months storage of the formulations at 25° C. and 60% RH. The 12 months results are described below.

Appearance

Appearance testing was performed visually on a single sample. The placebo sample was found to be a clear, colourless solution. The 0.5 mg/mL strength samples were a light yellow suspension free from visible agglomerates while the 2.5 mg/mL and 10 mg/mL strength samples appeared to be yellow suspensions free from visible agglomerates.

pH

The pH determination was performed on a single sample. The results are shown in Table 16.

TABLE 16

| Batch Number | Strength | pH |
|---|---|---|
| BN011/14 | 0.5 mg/mL | 6.656 |
| BN010/14 | 2.5 mg/mL | 6.652 |
| BN009/14 | 10 mg/mL | 6.655 |
| BN008/14 | Placebo | 6.661 |

All three active formulations and placebo were found to have a pH of 6.7 at the twelve month time-point. No change was observed from the initial time point.

Assay

Assay testing was performed in duplicate. The key method parameters are summarised as follows:

| | |
|---|---|
| Mobile phase | Acetonitrile:water:TFA 45:55:0.1 |
| Column | Waters X-Bridge phenyl, 3.5 µm, 150 × 4.6 mm, (Part Number 186003335) |
| Column temperature | 40° C. |
| Flow rate | 1.5 ml/min |
| Injection volume | 10 µl |
| Detection | UV, 254 nm |
| Runtime | 6 minutes |
| Autosampler temperature | Ambient |
| Standard Concentration | 0.1 mg/ml |

The results of the assay are shown in Table 17.

TABLE 17

| Batch Number | Strength | Prep 1 | Prep 2 | Mean |
|---|---|---|---|---|
| BN011/14 | 0.5 mg/mL | 0.5180 | 0.5178 | 0.52 |
| BN010/14 | 2.5 mg/mL | 2.6541 | 2.6407 | 2.65 |
| BN009/14 | 10 mg/mL | 10.4219 | 10.4926 | 10.46 |

The assay results for the active suspensions of each strength at the twelve month time point did not show any change from initial time point.

Related Substances

Related substances determination was performed in duplicate. The key method parameters are summarised as follows.

| | |
|---|---|
| Mobile phase | A - Purified water/Acetonitrile/TFA (95/5/0.1). B - Acetonitrile/Water/TFA (95/5/0.1). |
| Column | X-Bridge Phenyl 4.6 × 150 mm 3.5 µm particle size (ex - Waters; #186003335) |
| Column temperature | 30° C. |
| Autosampler Temperature | Ambient |
| Flow rate | 1.0 ml/min |
| Injection volume | 10 µl |
| Detection | UV, 254 nm |

| | Time (min) | % A | % B |
|---|---|---|---|
| Gradient | 0 | 100 | 0 |
| | 2 | 100 | 0 |
| | 15 | 0 | 100 |
| | 25 | 0 | 100 |
| | 27 | 100 | 0 |
| | 37 | 100 | 0 |

| | |
|---|---|
| Diluent | Acetonitrile:Water (50:50) |
| Sample Concentration | 0.2 mg/ml |
| Standard Concentration | 2 µg/ml |

The results from the related substances determination of the suspensions are presented in Table 18.

TABLE 18

Results from the related substances analysis of RPL554 suspensions (as % LC)

| RRT | % LC T1 | T2 | Mean |
|---|---|---|---|
| Batch BN011/14 - (0.5 mg/mL) - 25° C./60% RH | | | |
| 0.78 | 0.0776 | 0.0764 | 0.08 |
| 0.86 | 0.1028 | 0.1046 | 0.10 |
| 0.92 | 0.2084 | 0.2101 | 0.21 |
| 0.93 | 0.1875 | 0.1846 | 0.19 |
| 1.09 | 0.0548 | 0.0562 | 0.06 |
| 1.11 | 0.4130 | 0.4142 | 0.41 |
| Total | | | 1.05 |
| Batch BN010/14 - (2.5 mg/mL) - 25° C./60% RH | | | |
| 0.77 | 0.0779 | 0.0792 | 0.08 |
| 0.85 | 0.1041 | 0.1051 | 0.10 |
| 0.92 | 0.2184 | 0.2227 | 0.22 |
| 0.93 | 0.1768 | 0.1746 | 0.18 |
| 1.11 | 0.4226 | 0.4270 | 0.42 |
| Total | | | 1.00 |
| Batch BN009/14 - (10 mg/mL) - 25° C./60% RH | | | |
| 0.78 | 0.0769 | 0.0789 | 0.08 |
| 0.86 | 0.1016 | 0.1031 | 0.10 |
| 0.92 | 0.2056 | 0.2194 | 0.21 |
| 0.93 | 0.1819 | 0.1684 | 0.18 |
| 1.11 | 0.4137 | 0.4250 | 0.42 |
| Total | | | 0.99 |

The related substances results for the active suspensions of each strength at the twelve month time-point were similar to the initial time point.

Particle Size Distribution (PSD)

The Particle Size Distribution method was performed using a Spraytec with the settings detailed below.

Optical Properties: Particle: RI (real): 1.50 (standard opaque particle); RI (imaginary): 0.50; Density: 1.00; Dispersant (water); Dispersant RI: 1.33

Dispersant Used for Sample Analysis: 1% polysorbate 20 in deionised water

Controller Unit Settings: Stirrer speed 1000 rpm

Measurement Time: Sampling time: 30 s; Background time: 10 s

The results are shown in Table 19.

TABLE 19

Results from the Particle Size Determination by Laser Diffraction of RPL554 suspensions (in μm)

| Batch Number | Strength | Dv10 | Dv50 | Dv90 |
|---|---|---|---|---|
| BN011/14 | 0.5 mg/mL | 0.7946 | 1.577 | 3.168 |
| BN010/14 | 2.5 mg/mL | 0.7872 | 1.589 | 3.119 |
| BN009/14 | 10 mg/mL | 0.8012 | 1.566 | 2.976 |

The Particle Size Distribution profiles were similar for all 3 strengths at the twelve month time-point and did not show any change compared to the initial time point.

Microscopic Evaluation

Microscopic evaluation was performed by visually assessing the formulations using a G3 microscope. No aggregates were observed in any of the batches tested, although some large loose agglomerates were occasionally seen for the 2.5 mg/mL and 10 mg/mL suspensions. The evaluation determined that there was no change compared to the initial time point.

Delivery Rate and Total Delivered Dose

Delivery rate and total delivered dose was performed on 3 vials per batch. The suspensions were dispensed and delivered using a PARI LC PLUS® Nebuliser/PARI TurboBOY S® compressor combination. The results from the delivery rate and total delivered dose are presented in Table 20.

TABLE 20

Results from the delivery rate and total dose delivered determination using PARI LC PLUS nebuliser

| Replicate number | T1 | T2 | T3 |
|---|---|---|---|
| Batch BN011/14 0.5 mg/mL | | | |
| Initial weight (g) | 36.8175 | 36.7852 | 36.8030 |
| Final weight (g) | 32.6399 | 32.7369 | 32.6272 |
| Delivered mass (g) | 4.1776 | 4.0483 | 4.1758 |
| Total Delivery Time (s) | 900 | 1020 | 960 |
| Delivery Rate (mg/min) (over the first min) | 0.136 | 0.130 | 0.137 |
| Mean Delivery Rate (mg/min) | | 0.1 | |
| Assay* (mg) | 1.179 | 1.144 | 1.198 |
| Mean Assay* (mg) | | 1.2 | |
| % Efficiency | 54.50 | 54.56 | 55.39 |
| Mean % Efficiency | | 54.8 | |
| Batch BN010/14 2.5 mg/mL | | | |
| Initial weight (g) | 37.0977 | 38.7543 | 37.2942 |
| Final weight (g) | 32.8590 | 34.9311 | 32.9187 |
| Delivered mass (g) | 4.2387 | 4.3632 | 4.3755 |
| Total Delivery Time (s) | 1020 | 1020 | 1020 |
| Delivery Rate (mg/min) (over the first min) | 0.303 | 0.229 | 0.335 |
| Mean Delivery Rate (mg/min) | | 0.3 | |
| Assay* (mg) | 6.212 | 6.684 | 6.565 |
| Mean Assay* (mg) | | 6.5 | |
| % Efficiency | 55.36 | 57.86 | 56.68 |
| Mean % Efficiency | | 56.6 | |
| Batch BN009/14 10 mg/mL | | | |
| Initial weight (g) | 36.9365 | 38.4396 | 37.0922 |
| Final weight (g) | 32.6608 | 34.2031 | 32.7858 |
| Delivered mass (g) | 4.2757 | 4.2365 | 4.3064 |
| Total Delivery Time (s) | 1080 | 1140 | 1080 |
| Delivery Rate (mg/min) (over the first min) | 1.326 | 1.095 | 1.221 |
| Mean Delivery Rate (mg/min) | | 1.2 | |
| Assay* (mg) | 24.279 | 24.168 | 24.705 |
| Mean Assay* (mg) | | 24.4 | |
| % Efficiency | 54.30 | 54.55 | 54.86 |
| Mean % Efficiency | | 54.6 | |

*assay is total delivered
% Efficiency is total actual dose delivered/theoretical dose delivered (calculated using delivered mass and formulation strength from assay)

The total delivered dose and delivery rate for all strengths were similar to the initial time point. The delivery efficiency of all the suspensions was consistent with previous time points.

Aerodynamic Particle Size Distribution (APSD)

Aerodynamic Particle Size Distribution (APSD) determination was performed on 3 vials per batch per condition using the Next Generation Impactor (NGI). The suspensions were dispensed and delivered using a PARI LC PLUS® Nebuliser/PARI TurboBOY S® compressor combination. The results from the APSD determination are presented in Table 21. The results were input into the CITDAS program (Version 3.10) to calculate the fine particle dose using a cut-off value of 5 μm and the results obtained from the calculations are also presented Table 21.

TABLE 21

Results from the Aerodynamic Particle Size Distribution by NGI (as mg RPL554) using PARI LC PLUS nebuliser

| Stage | NGI 1 | NGI 2 | NGI 3 | Mean |
|---|---|---|---|---|
| Batch BN011/14 - (0.5 mg/mL) 25° C./60% RH ||||| 
| Throat | 0.05495 | 0.09324 | 0.08583 | 0.08 |
| Stage 1 | 0.13433 | 0.12798 | 0.12692 | 0.13 |
| Stage 2 | 0.26114 | 0.18827 | 0.22637 | 0.23 |
| Stage 3 | 0.40347 | 0.29208 | 0.39028 | 0.36 |
| Stage 4 | 0.49538 | 0.41178 | 0.46929 | 0.46 |
| Stage 5 | 0.23507 | 0.24668 | 0.29097 | 0.26 |
| Stage 6 | 0.07792 | 0.06313 | 0.08504 | 0.08 |
| Stage 7 | 0.01105 | 0.01100 | 0.01525 | 0.01 |
| MOC | 0.00034 | 0.00169 | 0.00151 | 0.00 |
| Sum | 1.67365 | 1.43585 | 1.69147 | 1.60 |
| Delivered Mass (g) | 4.2864 | 4.1465 | 4.2623 | 4.23 |
| FPD ≤5 μm* | 0.735 | 0.667 | 0.785 | 0.7 |
| FPD/delivered mass (mg/g) | 0.171 | 0.161 | 0.184 | 0.2 |
| FPF (FPD as % total dose) ≤5 μm* | 43.9 | 46.4 | 46.4 | 45.6 |
| GSD* | 2.0 | 2.2 | 2.0 | 2.1 |
| MMAD* | 5.3 | 5.0 | 5.1 | 5.2 |
| Batch BN010/14 - (2.5 mg/mL) 25° C./60% RH |||||
| Throat | 0.35731 | 0.43867 | 0.47848 | 0.42 |
| Stage 1 | 0.71616 | 1.04125 | 0.93292 | 0.90 |
| Stage 2 | 1.28121 | 1.58441 | 1.43900 | 1.43 |
| Stage 3 | 1.98259 | 2.21051 | 1.95403 | 2.05 |
| Stage 4 | 2.41709 | 2.37565 | 2.23993 | 2.34 |
| Stage 5 | 1.69766 | 1.45824 | 1.39429 | 1.52 |
| Stage 6 | 0.54927 | 0.43922 | 0.37542 | 0.45 |
| Stage 7 | 0.07994 | 0.07293 | 0.06443 | 0.07 |
| MOC | 0.00163 | 0.00151 | 0.00540 | 0.00 |
| Sum | 9.08286 | 9.62239 | 8.88390 | 9.20 |
| Delivered Mass (g) | 4.3881 | 4.5659 | 4.3137 | 4.42 |
| FPD ≤5 μm* | 4.356 | 3.945 | 3.702 | 4.0 |
| FPD/delivered mass (mg/g) | 0.993 | 0.864 | 0.858 | 0.9 |
| FPF (FPD as % total dose) ≤5 μm* | 48.0 | 41.0 | 41.7 | 43.5 |
| GSD* | 2.1 | 2.1 | 2.1 | 2.1 |
| MMAD* | 5.0 | 5.7 | 5.5 | 5.4 |
| Batch BN009/14 - (10 mg/mL) 25° C./60% RH |||||
| Throat | 1.82141 | 1.46478 | 1.70097 | 1.66 |
| Stage 1 | 2.99033 | 3.28692 | 3.75069 | 3.34 |
| Stage 2 | 5.51909 | 6.88069 | 7.01532 | 6.47 |
| Stage 3 | 8.46593 | 10.48679 | 10.09839 | 9.68 |
| Stage 4 | 9.42726 | 10.16201 | 9.36013 | 9.65 |
| Stage 5 | 6.30967 | 4.85282 | 4.67990 | 5.28 |
| Stage 6 | 1.84396 | 0.98008 | 1.00599 | 1.28 |
| Stage 7 | 0.28335 | 0.13666 | 0.12275 | 0.18 |
| MOC | 0.00383 | 0.00710 | 0.00108 | 0.00 |
| Sum | 36.66483 | 38.25785 | 37.73522 | 37.55 |
| Delivered Mass (g) | 4.3787 | 4.6309 | 4.4044 | 4.47 |
| FPD ≤5 μm* | 16.313 | 14.318 | 13.490 | 14.7 |
| FPD/delivered mass (mg/g) | 3.726 | 3.092 | 3.063 | 3.3 |
| FPF (FPD as % total dose) ≤5 μm* | 44.5 | 37.4 | 35.7 | 39.2 |
| GSD* | 2.0 | 1.9 | 1.9 | 2.0 |
| MMAD* | 5.3 | 5.9 | 6.1 | 5.8 |

*calculated using CITDAS on unrounded data.
Abbreviations:
FPD: fine particle dose;
FPF: fine particle fraction;
GSD: geometric size distribution;
MMAD: mass median aerodynamic diameter;
MOC: micro-orifice collector.

12 Months Stability

Tables 22 (for 0.5 mg/mL), 23 (for 2.5 mg/mL) and 24 (for 10 mg/mL) below combine the 12 months data described above with the corresponding data for the 1, 3 and 6 months time points for the RPL554 suspension formulations of the invention.

(Note: Impurity peaks marked with * in Tables 22, 23 and 24 were observed as a doublet but had been observed as a single peak at the initial time point. This is probably due to a new column being used which gave better separation and is not believed to be a sign of degradation.)

Summary

RPL554 Suspensions for Nebulisation 0.5 mg/mL (BN011/14), 2.5 mg/mL (BN010/14) and 10 mg/mL (BN009/14) and associated placebo (BN008/14) were manufactured and placed on stability at 25° C./60% RH and were tested at the 12 month time-point.

The results showed that there was essentially no change in any of the batches tested at the 12 month time point and confirmed that the RPL554 suspensions for nebulisation were stable for 12 months at 25° C./60% RH.

TABLE 22

| (0.5 mg/mL) Test | Initial | 1 month | 3 month | 6 month | 12 month |
|---|---|---|---|---|---|
| Storage condition | N/A | 25° C./60% RH | 25° C./60% RH | 25° C./60% RH | 25° C./60% RH |
| Appearance | Pale yellow suspensions free from visible agglomerates | Pale yellow suspensions free from visible agglomerates | Pale yellow suspensions free from visible agglomerates | Pale yellow suspensions free from visible agglomerates | Pale yellow suspensions free from visible agglomerates |
| pH | 6.7 | 6.7 | 6.6 | 6.6 | 6.7 |
| Mean Assay (n = 2) (mg/mL) | 0.51 | 0.51 | 0.52 | 0.52 | 0.52 |
| Mean Impurities (n = 2) (% LC) | | | | | |
| Total | 0.98 | 1 | 0.89 | 0.95 | 1.05 |
| Greatest | 0.39 (RRT 1.11) | 0.23 (RRT 0.92) | 0.38 (RRT 1.10) | 0.38 (RRT 1.10) | 0.41 (RRT 1.11) |
| Second greatest | 0.23 (RRT 0.92) | 0.20 (RRT 1.11)* 0.18 (RRT 1.10)* | 0.22 (RRT 0.92) | 0.22 (RRT 0.93) | 0.21 (RRT 0.92) |
| PSD (μm) | Dv10 = 0.7646 Dv50 = 1.534 Dv90 = 2.999 | Dv10 = 0.7721 Dv50 = 1.542 Dv90 = 2.991 | Dv10 = 0.7823 Dv50 = 1.56 Dv90 = 3.084 | Dv10 = 0.8036 Dv50 = 1.585 Dv90 = 3.158 | Dv10 = 0.7946 Dv50 = 1.577 Dv90 = 3.168 |
| Mean FPD (mg) | 0.4 | 0.6 | 0.6 | 0.6 | 0.7 |
| Mean FPD/mass delivered (n = 3) (mg/g) | 0.1 | 0.2 | 0.1 | 0.1 | 0.2 |

TABLE 22-continued

| (0.5 mg/mL) Test | Initial | 1 month | 3 month | 6 month | 12 month |
|---|---|---|---|---|---|
| Mean MMAD (n = 3) | 5.4 | 5.7 | 5.4 | 5.6 | 5.2 |
| Mean GSD (n = 3) | 2 | 2 | 2.1 | 2 | 2.1 |
| Mean vial fill weight (n = 5) (g) | 5.0 (n = 10) | 5.1 | 5.1 | 5.1 | 5.1 |
| Mean Total delivered dose (n = 3) (mg) | 1.1 | 1.1 | 1.2 (n = 5) | 1 | 1.2 |
| Mean Delivery rate (n = 3) (mg/min) (over first two min) | 0.1 | 0.1 | 0.1 (n = 5) | 0.1 | 0.1 |
| Mean % Efficiency (n = 3) | 53.8 | 55.5 | 56.0 (n = 5) | 51.4 | 54.8 |

TABLE 23

| (2.5 mg/mL) Test | Initial | 1 month | 3 month | 6 month | 12 month |
|---|---|---|---|---|---|
| Storage condition | N/A | 25° C./60% RH | 25° C./60 RH | 25° C./60% RH | 25° C./60% RH |
| Appearance | Yellow suspension free from visible agglomerates | Yellow suspension free from visible agglomerates | Yellow suspension free from visible agglomerates | Yellow suspension free from visible agglomerates | Yellow suspension free from visible agglomerates |
| pH | 6.7 | 6.7 | 6.7 | 6.6 | 6.7 |
| Mean Assay (n = 2) (mg/g) | 2.6 | 2.57 | 2.64 | 2.63 | 2.65 |
| Mean Impurities (n = 2) (% LC) | | | | | |
| Total | 1.02 | 0.92 | 0.89 | 0.98 | 1 |
| Greatest | 0.41 (RRT 1.10) | 0.23 (RRT 0.92) | 0.39 (RRT 1.10) | 0.41 (RRT 1.10) | 0.42 (RRT 1.11) |
| Second greatest | 0.23 (RRT 0.92) | 0.20 (RRT 1.11)* 0.18 (RRT 1.10)* | 0.22 (RRT 0.93) | 0.23 (RRT 0.93) | 0.22 (RRT 0.92) |
| PSD (μm) | Dv10 = 0.7964 Dv50 = 1.586 Dv90 = 3.075 | Dv10 = 0.7981 Dv50 = 1.569 Dv90 = 3 | Dv10 = 0.7943 Dv50 = 1.561 Dv90 = 2.98 | Dv10 = 0.7851 Dv50 = 1.583 Dv90 = 3.099 | Dv10 = 0.7872 Dv50 = 1.589 Dv90 = 3.119 |
| Mean FPD (mg) | 3 | 3.1 | 3.4 | 3.5 | 4 |
| Mean FPD/mass delivered (n = 3) (mg/g) | 0.7 | 0.7 | 0.8 | 0.8 | 0.9 |
| Mean MMAD (n = 3) | 6.0 | 6.1 | 5.8 | 6 | 5.4 |
| Mean GSD (n = 3) | 1.9 | 1.9 | 1.9 | 2 | 2.1 |
| Mean Vial Content Uniformity (n = 10) | Pass EP 2.9.6 and 2.9.40 | N/A | N/A | N/A | N/A |
| Mean vial fill weight (n = 5) (g) | 5.1 (n = 10) | 5.2 | 5.2 | 5.3 | 5.3 |
| Mean Total delivered dose (n = 3) (mg) | 6 | 6.2 | 4.5 | 5.7 | 6.5 |
| Mean Delivery rate (n = 3) (mg/min) (over the first min) | 0.3 | 0.3 | 0.2 | 0.3 | 0.3 |
| Mean % Efficiency (n = 3) | 56.3 | 55.5 | 41.2 | 55 | 56.6 |

TABLE 24

| (10 mg/mL) Test | Initial | 1 month | 3 month | 6 month | 12 month |
|---|---|---|---|---|---|
| Storage condition | N/A | 25° C./60% RH | 25° C./60% RH | 25° C./60 RH | 25° C./60% RH |
| Appearance | Yellow suspension free from visible agglomerates | Yellow suspension free from visible agglomerates | Yellow suspension free from visible agglomerates | Yellow suspension free from visible agglomerates | Yellow suspension free from visible agglomerates |
| pH | 6.7 | 6.7 | 6.7 | 6.6 | 6.7 |
| Mean Assay (n = 2) (mg/mL) | 10.24 | 10.16 | 10.28 | 10.23 | 10.46 |
| Mean Impurities (n = 2) (% LC) | | | | | |
| Total | 0.98 | 0.92 | 0.89 | 0.97 | 0.99 |
| Greatest | 0.40 (RRT 1.11) | 0.23 (RRT 0.92) | 0.39 (RRT 1.10) | 0.41 (RRT 1.10) | 0.42 (RRT 1.11) |
| Second greatest | 0.23 (RRT 0.92) | 0.21 (RRT 1.11)* 0.18 (RRT 1.10)* | 0.22 (RRT 0.93) | 0.22 (RRT 0.93) | 0.21 (RRT 0.92) |
| PSD (μm) | Dv10 = 0.7884 Dv50 = 1.564 Dv90 = 3.02 | Dv10 = 0.7877 Dv50 = 1.55 Dv90 = 2.965 | Dv10 = 0.7954 Dv50 = 1.545 Dv90 = 2.909 | Dv10 = 0.7756 Dv50 = 1.558 Dv90 = 3.059 | Dv10 = 0.8012 Dv50 = 1.566 Dv90 = 2.976 |
| Mean FPD (mg) | 12.2 | 12.7 | 14.2 | 13.3 | 14.7 |
| Mean FPD/mass delivered (n = 3) (mg/g) | 2.9 | 3 | 3.1 | 2.2 (n=2) | 3.3 |
| Mean MMAD (n = 3) | 6.1 | 5.9 | 6 | 5.7 (n=2) | 5.8 |
| Mean GSD (n = 3) | 1.9 | 1.9 | 1.9 | 2.0 (n=2) | 2 |

TABLE 24-continued

| (10 mg/mL) Test | Initial | 1 month | 3 month | 6 month | 12 month |
|---|---|---|---|---|---|
| Mean Vial Content Uniformity (n = 10) | Pass EP 2.9.6 and 2.9.40 | N/A | N/A | N/A | N/A |
| Mean vial fill weight (n = 5) (g) | 5.2 (n = 10) | 5.1 | 5.1 | 5.1 | 5.1 |
| Mean Total delivered dose (n = 3) (mg) | 25.5 | 23.4 | 26.4 | 22.7 | 24.4 |
| Mean Delivery rate (n = 3) (mg/min) (over the first min) | 1.3 | 1.4 | 1.4 | 1.2 | 1.2 |
| Mean % Efficiency (n = 3) | 57.3 | 52.8 | 56.7 | 53.5 | 54.6 |

Example 9

Six Month Analysis at Accelerated Conditions (40° C./75% RH)

Accelerated stability studies at 40° C./75% RH were also continued to the sixth month. The results of these are shown in Table 25 (for 0.5 mg/mL), Table 26 (for 2.5 mg/mL) and Table 27 (for 10 mg/mL).

(As noted in Example 8, impurity peaks marked with * were observed as a doublet but had been observed as a single peak at the initial time point. This is probably due to a new column being used which gave better separation and is not believed to be a sign of degradation.)

The results showed that there was essentially no change in any of the batches tested at the 6 month time point and confirmed that the RPL554 suspensions for nebulisation have excellent stability, being stable for 6 months at 40° C./75% RH.

TABLE 25

| (0.5 mg/mL) Test | Initial | 1 month | 3 month | 6 month |
|---|---|---|---|---|
| Storage condition | N/A | 40° C./75% RH | 40° C./75% RH | 40° C./75% RH |
| Appearance | Pale yellow suspensions free from visible agglomerates | Pale yellow suspensions free from visible agglomerates | Pale yellow suspensions free from visible agglomerates | Pale yellow suspensions free from visible agglomerates |
| pH | 6.7 | 6.7 | 6.6 | 6.6 |
| Mean Assay (n = 2) (mg/mL) | 0.51 | 0.51 | 0.52 | 0.52 |
| Mean Impurities (n = 2) (% LC) | | | | |
| Total | 0.98 | 0.9 | 0.9 | 0.98 |
| Greatest | 0.39 (RRT 1.11) | 0.23 (RRT 0.92) | 0.37 (RRT 1.10) | 0.37 (RRT 1.10) |
| Second greatest | 0.23 (RRT 0.92) | 0.20 (RRT 1.11)* 0.18 (RRT 1.10)* | 0.22 (RRT 0.92) | 0.22 (RRT 0.93) |
| PSD (μm) | Dv10 = 0.7646 Dv50 = 1.534 Dv90 = 2.999 | Dv10 = 0.7902 Dv50 = 1.56 Dv90 = 3.026 | Dv10 = 0.7749 Dv50 = 1.586 Dv90 = 3.335 | Dv10 = 0.8324 Dv50 = 1.573 Dv90 = 2.899 |
| Mean FPD (mg) | 0.4 | 0.6 | 0.7 | 0.6 |
| Mean FPD/mass delivered (n = 3) (mg/g) | 0.1 | 0.2 | 0.2 | 0.1 |
| Mean MMAD (n = 3) | 5.4 | 5.8 | 5.3 | 5.5 |
| Mean GSD (n = 3) | 2 | 1.9 | 2 | 2.1 |
| Mean Vial Content Uniformity (n = 10) | Pass EP 2.9.6 and 2.9.40 | N/A | N/A | N/A |
| Mean vial fill weight (n = 5) (g) | 5.0 (n = 10) | 5.1 | 5.1 | 5.1 |
| Mean Total delivered dose (n = 3) (mg) | 1.1 | 1.1 | 1.2 | 1.1 |
| Mean Delivery rate (n = 3) (mg/min) (over first two min) | 0.1 | 0.1 | 0.1 | 0.1 |
| Mean % Efficiency (n = 3) | 53.8 | 55.1 | 54.3 | 53.4 |

TABLE 26

| (2.5 mg/mL) Test | Initial | 1 month | 3 month | 6 month |
|---|---|---|---|---|
| Storage condition | N/A | 40° C./75% RH | 40° C./75% RH | 40° C./75% RH |
| Appearance | Yellow suspension free from visible agglomerates | Yellow suspension free from visible agglomerates | Yellow suspension free from visible agglomerates | Yellow suspension free from visible agglomerates |
| pH | 6.7 | 6.7 | 6.6 | 6.6 |
| Mean Assay (n = 2) (mg/mL) | 2.6 | 2.58 | 2.64 | 2.63 |
| Mean Impurities (n = 2) (% LC) | | | | |
| Total | 1.02 | 0.92 | 0.9 | 0.99 |
| Greatest | 0.41 (RRT 1.10) | 0.23 (RRT 0.92) | 0.38 (RRT 1.10) | 0.40 (RRT 1.10) |
| Second greatest | 0.23 (RRT 0.92) | 0.20 (RRT 1.11)* 0.18 (RRT 1.10)* | 0.22 (RRT 0.93) | 0.23 (RRT 0.93) |
| PSD (μm) | Dv10 = 0.7964 Dv50 = 1.586 Dv90 = 3.075 | Dv10 = 0.7861 Dv50 = 1.563 Dv90 = 3.023 | Dv10 = 0.7994 Dv50 = 1.577 Dv90 = 3.058 | Dv10 = 0.7997 Dv50 = 1.614 Dv90 = 3.183 |
| Mean FPD (mg) | 3 | 3.2 | 3.6 | 3.6 |
| Mean FPD/mass delivered (n = 3) (mg/g) | 0.7 | 0.8 | 0.8 | 0.8 |
| Mean MMAD (n = 3) | 6 | 6 | 5.7 | 5.9 |
| Mean GSD (n = 3) | 1.9 | 1.9 | 2 | 2 |
| Mean Vial Content Uniformity (n = 10) | Pass EP 2.9.6 and 2.9.40 | N/A | N/A | N/A |
| Mean vial fill weight (n = 5) (g) | 5.1 (n = 10) | 5.3 | 5.3 | 5.3 |
| Mean Total delivered dose (n = 3) (mg) | 6 | 6.1 | 5.6 | 6.4 |
| Mean Delivery rate (n = 3) (mg/min) (over the first min) | 0.3 | 0.3 | 0.3 | 0.4 |
| Mean % Efficiency (n = 3) | 56.3 | 56.1 | 50.5 | 56.3 |

TABLE 27

| (10 mg/mL) Test | Initial | 1 month | 3 month | 6 month |
|---|---|---|---|---|
| Storage condition | N/A | 40° C./75% RH | 40° C./75% RH | 40° C./75% RH |
| Appearance | Yellow suspension free from visible agglomerates | Yellow suspension free from visible agglomerates | Yellow suspension free from visible agglomerates | Yellow suspension free from visible agglomerates |
| pH | 6.7 | 6.7 | 6.6 | 6.6 |
| Mean Assay (n = 2) (mg/mL) | 10.24 | 10.1 | 10.41 | 10.37 |
| Mean Impurities (n = 2) (% LC) | | | | |
| Total | 0.98 | 0.97 | 0.89 | 0.98 |
| Greatest | 0.40 (RRT 1.11) | 0.23 (RRT 0.92) | 0.38 (RRT 1.10) | 0.40 (RRT 1.10) |
| Second greatest | 0.23 (RRT 0.92) | 0.21 (RRT 1.11)* 0.18 (RRT 1.10)* | 0.23 (RRT 0.93) | 0.23 (RRT 0.93) |
| PSD (μm) | Dv10 = 0.7884 Dv50 = 1.564 Dv90 = 3.02 | Dv10 = 0.7906 Dv50 = 1.554 Dv90 = 2.971 | Dv10 = 0.7882 Dv50 = 1.565 Dv90 = 3.024 | Dv10 = 0.7757 Dv50 = 1.553 Dv90 = 3.015 |
| Mean FPD (mg) | 12.2 | 13.1 | 14.5 | 13.4 |
| Mean FPD/mass delivered (n = 3) (mg/g) | 2.9 | 3.1 | 3.4 | 3.1 |
| Mean MMAD (n = 3) | 6.1 | 5.8 | 5.8 | 5.7 |

TABLE 27-continued

| (10 mg/mL) Test | Initial | 1 month | 3 month | 6 month |
|---|---|---|---|---|
| Mean GSD (n = 3) | 1.9 | 1.9 | 2 | 2 |
| Mean Vial Content Uniformity (n = 10) | Pass EP 2.9.6 and 2.9.40 | N/A | N/A | N/A |
| Mean vial fill weight (n = 5) (g) | 5.2 (n = 10) | 5.2 | 5.1 | 5.1 |
| Mean Total delivered dose (n = 3) (mg) | 25.5 | 24.1 | 26.9 | 22.8 |
| Mean Delivery rate (n = 3) (mg/min) (over the first min) | 1.3 | 1.3 | 1.2 | 1.3 |
| Mean % Efficiency (n = 3) | 57.3 | 54.3 | 56.2 | 51.6 |

The invention claimed is:

1. A liquid pharmaceutical composition suitable for administration by inhalation comprising a diluent and a suspension of particles of 9,10-dimethoxy-2-(2,4,6-trimethylphenylimino)-3-(N-carbamoyl-2-aminoethyl)-3,4,6,7-tetrahydro-2H-pyrimido[6,1-a]isoquinolin-4-one (RPL554) or a pharmaceutically acceptable salt thereof, wherein the particles of RPL554 have a particle size distribution with a Dv50 (median particle size by volume) value of from about 0.2 μm to about 5 μm.

2. A liquid pharmaceutical composition according to claim 1, wherein the particles of RPL554 have a particle size distribution with a Dv50 value of from about 0.7 μm to about 2.5 μm.

3. A liquid pharmaceutical composition according to claim 1, wherein the concentration of particles of RPL554 in the liquid pharmaceutical composition is from about 0.01 mg/mL to about 40 mg/mL.

4. A liquid pharmaceutical composition according to claim 1, wherein the composition has a pH of from about 6 to about 8.

5. A liquid pharmaceutical composition according to claim 1 which further comprises one or more surfactants.

6. A liquid pharmaceutical composition according to claim 5, wherein the one or more surfactants are selected from one or more non-ionic surfactants.

7. A liquid pharmaceutical composition according to claim 6, wherein the one or more surfactants are selected from polyoxyethylene glycol sorbitan alkyl esters and sorbitan alkyl esters.

8. A liquid pharmaceutical composition according to claim 1 which further comprises one or more buffers.

9. A liquid pharmaceutical composition according to claim 8, wherein the one or more buffers are selected from citrate or phosphate buffers.

10. A liquid pharmaceutical composition according to claim 1, which composition comprises:
   (a) the particles of RPL554 at a concentration of from about 0.01 mg/mL to about 40 mg/mL;
   (b) one or more surfactants at a concentration of from about 0.01 mg/mL to about 5 mg/mL; and
   (c) a buffer at a concentration of from about 5 mg/mL to about 20 mg/mL.

11. A liquid pharmaceutical composition according to claim 1, wherein the composition further comprises a tonicity adjuster, optionally wherein the tonicity adjuster is sodium chloride.

12. A liquid pharmaceutical composition according to claim 1, wherein the diluent is water.

13. A liquid pharmaceutical composition according to claim 1, which composition comprises:
   (a) the particles of RPL554 at a concentration of 0.01 mg/mL to 30 mg/mL;
   (b) a polyoxyethylene glycol sorbitan alkyl ester at a concentration of from 0.1 mg/mL to 2 mg/mL;
   (c) a sorbitan alkyl ester at a concentration of from 0.01 mg/mL to 0.1 mg/mL;
   (d) a first phosphate buffer component at a concentration of from 5 mg/mL to 10 mg/mL;
   (e) a second phosphate buffer component at a concentration of from 5 mg/mL to 10 mg/mL; and
   (f) a tonicity adjuster at a concentration of from 2 mg/mL to 8 mg/mL.

14. A liquid pharmaceutical composition according to claim 1, which composition comprises:
   (a) the particles of RPL554 at a concentration of 0.05 mg/mL to 25 mg/mL;
   (b) polyoxyethylene (20) sorbitan monolaurate (Polysorbate 20, Tween 20) at a concentration of from 0.1 mg/mL to 2 mg/mL;
   (c) sorbitan monolaurate (Span 20) at a concentration of from 0.01 mg/mL to 0.1 mg/mL;
   (d) monosodium phosphate monohydrate at a concentration of from 5 mg/mL to 10 mg/mL;
   (e) dibasic sodium phosphate anhydrous at a concentration of from 5 mg/mL to 10 mg/mL; and
   (f) sodium chloride at a concentration of from 2 mg/mL to 8 mg/mL.

15. A liquid pharmaceutical composition according to claim 1 which is suitable for administration by nebulizer.

16. A nebulizer comprising a composition according to claim 1.

17. A method of treating a disease or condition selected from asthma, allergic asthma, hay fever, allergic rhinitis, bronchitis, emphysema, bronchiectasis, chronic obstructive pulmonary disease (COPD), adult respiratory distress syndrome (ARDS), steroid resistant asthma, severe asthma, paediatric asthma, cystic fibrosis, lung fibrosis, pulmonary fibrosis, interstitial lung disease, skin disorders, atopic dermatitis, psoriasis, ocular inflammation, cerebral ischaemia, inflammatory diseases and auto-immune diseases in a subject, which method comprises administering to said subject an effective amount of a liquid pharmaceutical composition according to claim 1.

18. A method of treating a disease or condition according to claim 17, wherein the disease or condition is chronic obstructive pulmonary disease (COPD).

\* \* \* \* \*